(12) United States Patent
Suzuki et al.

(10) Patent No.: US 8,078,269 B2
(45) Date of Patent: Dec. 13, 2011

(54) APPARATUS, METHOD AND SYSTEM OF MEASURING SLEEP STATE

(75) Inventors: Takuji Suzuki, Kanagawa (JP);
Kazushige Ouchi, Kanagawa (JP);
Kenichi Kameyama, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1058 days.

(21) Appl. No.: 11/532,770

(22) Filed: Sep. 18, 2006

(65) Prior Publication Data

US 2007/0106183 A1 May 10, 2007

(30) Foreign Application Priority Data

Nov. 9, 2005 (JP) ................................. 2005-325388

(51) Int. Cl.
*A61B 5/0205* (2006.01)
(52) U.S. Cl. ...................... 600/513; 600/509; 600/515
(58) Field of Classification Search .................. 600/509, 600/513, 515
See application file for complete search history.

(56) References Cited

U.S. PATENT DOCUMENTS

| | | | | |
|---|---|---|---|---|
| 5,902,250 | A * | 5/1999 | Verrier et al. | ................. 600/515 |
| 2005/0234314 | A1 | 10/2005 | Suzuki et al. | |
| 2006/0189855 | A1 | 8/2006 | Moriya et al. | |
| 2006/0241506 | A1* | 10/2006 | Melker et al. | ................. 600/529 |

FOREIGN PATENT DOCUMENTS

| | | |
|---|---|---|
| JP | 6-98863 | 4/1994 |
| JP | 7-143972 | 6/1995 |
| JP | 2002-34955 | 2/2002 |
| JP | 2002-63278 | 2/2002 |
| JP | 2002-219116 | 8/2002 |
| JP | 2002-291710 | 10/2002 |
| JP | 2004-126722 | 4/2004 |
| JP | 2004-344265 | 12/2004 |
| JP | 2005-198829 | 7/2005 |
| JP | 2005-279113 | 10/2005 |
| WO | WO 2004/078132 A2 | 9/2004 |

OTHER PUBLICATIONS

U.S. Appl. No. 12/036,740, filed Feb. 25, 2008, Suzuki, et al.
U.S. Appl. No. 11/689,126, filed Mar. 21, 2007, Suzuki, et al.
U.S. Appl. No. 12/212,182, filed Sep. 17, 2008, Suzuki.
U.S. Appl. No. 11/854,935, filed Sep. 13, 2007, Moriya, et al.

* cited by examiner

*Primary Examiner* — Niketa Patel
*Assistant Examiner* — Rex R Holmes
(74) *Attorney, Agent, or Firm* — Oblon, Spivak, McClelland, Maier & Neustadt, L.L.P.

(57) ABSTRACT

A sleep state measuring apparatus includes an autonomic nerve index obtaining unit that obtains a user's autonomic nerve index; and a sleep periodicity index calculating unit that calculates a sleep periodicity index based on a temporal change of the autonomic nerve index and a change in a user's sleeping cycle, wherein the sleep periodicity index indicates whether the user is sleeping or not according to a user's ideal sleeping cycle as an index, or a dominance index calculating unit that calculates a parasympathetic nerve dominance index which shows dominance of a parasympathetic nerve index included in the autonomic nerve index with respect to a sympathetic nerve index included in the autonomic nerve index for a user during sleep.

12 Claims, 15 Drawing Sheets

FIG.9

|  | MEASUREMENT RESULT (USER A) |
|---|---|
| SLEEP TIME | 6:22:30 |
| BEDTIME | 0:28:20 |
| RISING TIME | 7:13:50 |
| SLEEP EFFICIENCY (%) | 90.96667 |
| HEELING DEGREE | 9.233333 |
| AMOUNT OF BODY MOVEMENT | 1.168833 |
| SLEEPING RHYTHM INDEX | 230.9333 |
| SLEEP ONSET LATENCY (MINUTE) | 14.16667 |
| NUMBER OF AROUSAL DURING SLEEP (TIMES) | 10.66667 |
| TIME OF AROUSAL DURING SLEEP (MINUTE) | 29.83333 |

APPARATUS, METHOD AND SYSTEM OF MEASURING SLEEP STATE

This application is based upon and claims the benefit of priority from the prior Japanese Patent Application No. 2005-325388, filed on Nov. 9, 2005; the entire contents of which are incorporated herein by reference.

BACKGROUND OF THE INVENTION

1. Field of the Invention

The present invention relates to an apparatus, a method, and a system of measuring a sleep state, which obtain indexes indicating a user's sleep state.

2. Description of the Related Art

Conventionally, a sleep state measuring apparatus that determines a subject's sleep state based on pulse interval data, that is, data set of interval of a subject's pulse wave, and body movement data exhibiting the subject's body movement has been researched and developed. As compared with a large-sized apparatus that automatically determines a sleep state based on patterns of biosignals such as brain waves, eye movement, electromyogram, electrocardiogram, and the like, called a sleep polygraph, the sleep state measuring apparatus has received attention as a sleep state measuring apparatus that is capable of easily determining a sleep state on a daily life.

The sleep state measuring apparatus considers a pulsating interval of heart beats, that is, an activity of an autonomic nerve during sleep, as a pulse interval of a pulse wave so as to determine a sleep state based on an autonomic nerve index obtained from fluctuation in the pulse interval. For example, because a pulse wave, that is, a change in the bloodstream of blood vessels of hands, changes in synchronization with heart beats, it is possible to obtain a pulsating interval of the heart beats based on a pulse interval of a pulse wave. In the related art, such as JP-A 2002-291710 (KOKAI) and JP-A 7-143972 (KOKAI), a sleep state is determined based on an autonomic nerve index obtained from a frequency spectrum component of pulse wave data. That is, a series of pulse interval data is obtained from pulse wave data and the series of pulse interval data is converted into frequency spectrum distribution. Further, an autonomic nerve index is obtained from values of power spectrums in a low-frequency region (around 0.05 to 0.15 Hz) and a high-frequency region (around 0.15 to 0.4 Hz), which are obtained from the series of pulse interval data converted into the frequency spectrum distribution, thereby determining a sleep state according to the autonomic nerve index. In addition, in the related art, as disclosed in JP-A No. 2002-34955, body movement data in addition to pulse wave data is measured, thereby determining a sleep state, such as awakening, REM sleep, non-REM sleep, arousal during sleeparousal during sleep and the like.

In the related art of the first to third documents, it is possible to determine a sleep state, such as awakening, REM sleep, non-REM sleep, arousal during sleep, and the like. However, despite the fact that an object is to easily measure a sleep state on a daily life, it is only the time series variation of the sleep state that is finally displayed. Further, even though general users refer to the time series variation in the sleep state, it is difficult to determine so-called sleeping quality, for example, whether the users sleep deeply or lightly.

In addition, in order for the user to determine sleeping quality, a sleep state needs to be shown as an index. However, because absolute standard is hard to be set due to a wide variation between individuals, it is difficult to evaluate sleeping quality.

SUMMARY OF THE INVENTION

According to one aspect of the present invention, a sleep state measuring apparatus includes an autonomic nerve index obtaining unit that obtains a user's autonomic nerve index; and a sleep periodicity index calculating unit that calculates a sleep periodicity index based on a temporal change of the autonomic nerve index and a change in a user's sleeping cycle, wherein the sleep periodicity index indicates whether the user is sleeping or not according to a user's ideal sleeping cycle as an index.

According to another aspect of the present invention, a sleep state measuring apparatus includes an autonomic nerve index obtaining unit that obtains a user's autonomic nerve index; and a dominance index calculating unit that calculates a parasympathetic nerve dominance index which shows dominance of a parasympathetic nerve index included in the autonomic nerve index with respect to a sympathetic nerve index included in the autonomic nerve index for a user during sleep.

According to still another aspect of the present invention, a method of measuring a sleep state includes obtaining a user's autonomic nerve index; and calculating a sleep periodicity index based on a temporal change of the autonomic nerve index and a change in a user's sleeping cycle, wherein the sleep periodicity index indicates whether the user is sleeping or not according to a user's ideal sleeping cycle as an index.

According to still another aspect of the present invention, a method of measuring a sleep state includes obtaining a user's autonomic nerve index; and calculating a parasympathetic nerve dominance index which shows dominance of a parasympathetic nerve index included in the autonomic nerve index with respect to a sympathetic nerve index included in the autonomic nerve index for a user during sleep.

According to still another aspect of the present invention, a system of measuring a sleep state includes a sleep state measuring apparatus that performs a measuring to a user; and an information processing apparatus that communicates with the sleep state measuring apparatus, wherein the sleep state measuring apparatus includes: an autonomic nerve index obtaining unit that obtains a user's autonomic nerve index; and a data transmitting unit that transmits the autonomic nerve index, and the information processing apparatus includes: a data receiving unit that receives the autonomic nerve index; and a sleep periodicity index calculating unit that calculates a sleep periodicity index based on a temporal change of the autonomic nerve index and a change in a user's sleeping cycle, wherein the sleep periodicity index indicates whether the user is sleeping or not according to a user's ideal sleeping cycle as an index.

According to still another aspect of the present invention, a system of measuring a sleep state includes a sleep state measuring apparatus that performs a measuring to a user; and an information processing apparatus that communicates with the sleep state measuring apparatus, wherein the sleep state measuring apparatus includes: an autonomic nerve index obtaining unit that obtains a user's autonomic nerve index; and a data transmitting unit that transmits the autonomic nerve index, and the information processing apparatus includes: a data receiving unit that receives the autonomic nerve index; and a dominance index calculating unit that calculates a parasympathetic nerve dominance index which shows dominance of a parasympathetic nerve index included in the autonomic nerve index with respect to a sympathetic nerve index included in the autonomic nerve index for a user during sleep.

BRIEF DESCRIPTION OF THE DRAWINGS

FIG. 9 is a view illustrating an example of indexes indicating a sleep state, which can be obtained by the sleep state measuring apparatus according to the first embodiment that measures overnight sleeping of a user A;

DETAILED DESCRIPTION OF THE INVENTION

Hereinafter, the preferred embodiments of an apparatus, a method, and a system of measuring a sleep state according to the present invention will be described in detail with reference to the accompanying drawings. A sleep state measuring apparatus according to a first embodiment is used to measure a sleep state based on a photoelectric pulse wave of a finger and the acceleration of a wrist, which are measured by an arm-mounted type sensor module. A sleep state measuring system according to a second embodiment is used when a sleep state measuring apparatus obtains a photoelectric pulse wave of a finger and the acceleration of a wrist by an arm-mounted type sensor module so as to obtain an autonomic nerve index, and a PC measures a sleep state according to the autonomic nerve index. A sleep state measuring apparatus according to a third embodiment is used to measure a sleep state based on heart beats and body movement, which are detected by a mat-type sensor module by measuring vibration of the chest or the abdomen by a pressure sensor. A sleep state measuring apparatus according to a fourth embodiment is used to measure a sleep state based on heart beats and body movement, which are detected based on a differential image of a blanket by a camera.

Figure 1:
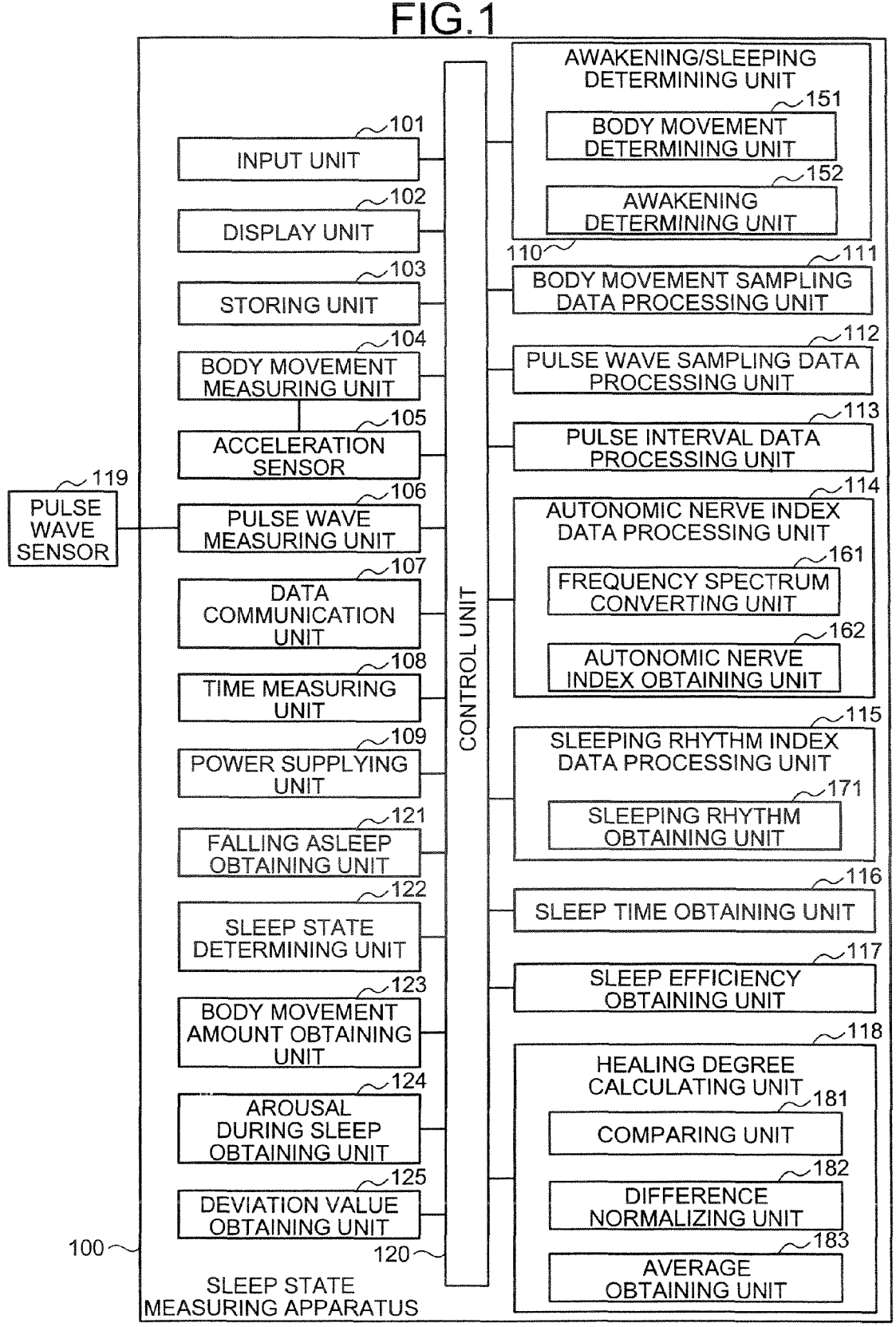
FIG. 1 is a block diagram illustrating a configuration of a sleep state measuring apparatus according to a first embodiment.

In the first embodiment, when a wristwatch-type sensor module is used in the sleep state measuring apparatus, body movement is measured by using an acceleration sensor and a pulse is obtained by a photoelectric pulse wave sensor mounted on a finer, thereby measuring an autonomic nerve index. FIG. 1 is a block diagram illustrating a sleep state measuring apparatus 100 according to the first embodiment. As shown therein, the sleep state measuring apparatus 100 includes an input unit 101, a display unit 102, a storing unit 103, a body movement measuring unit 104, an acceleration sensor 105, a pulse wave measuring unit 106, a data communication unit 107, a time measuring unit 108, a power supplying unit 109, an awakening/sleeping determining unit 110, a body movement sampling data processing unit 111, a pulse wave sampling data processing unit 112, a pulse interval data processing unit 113, an autonomic nerve index data processing unit 114, a sleeping rhythm index data processing unit 115, a sleep time obtaining unit 116, a sleep efficiency obtaining unit 117, a healing degree calculating unit 118, a control unit 120, a falling asleep obtaining unit 121, a sleep state determining unit 122, a body movement amount obtaining unit 123, an arousal during sleep obtaining unit 124, and a deviation value obtaining unit 125. The sleep state measuring apparatus 100 according to the present embodiment analyzes the measured data, accumulates the analyzed result in the storing unit 103, and displays the same on the display unit 102.

Figure 2:
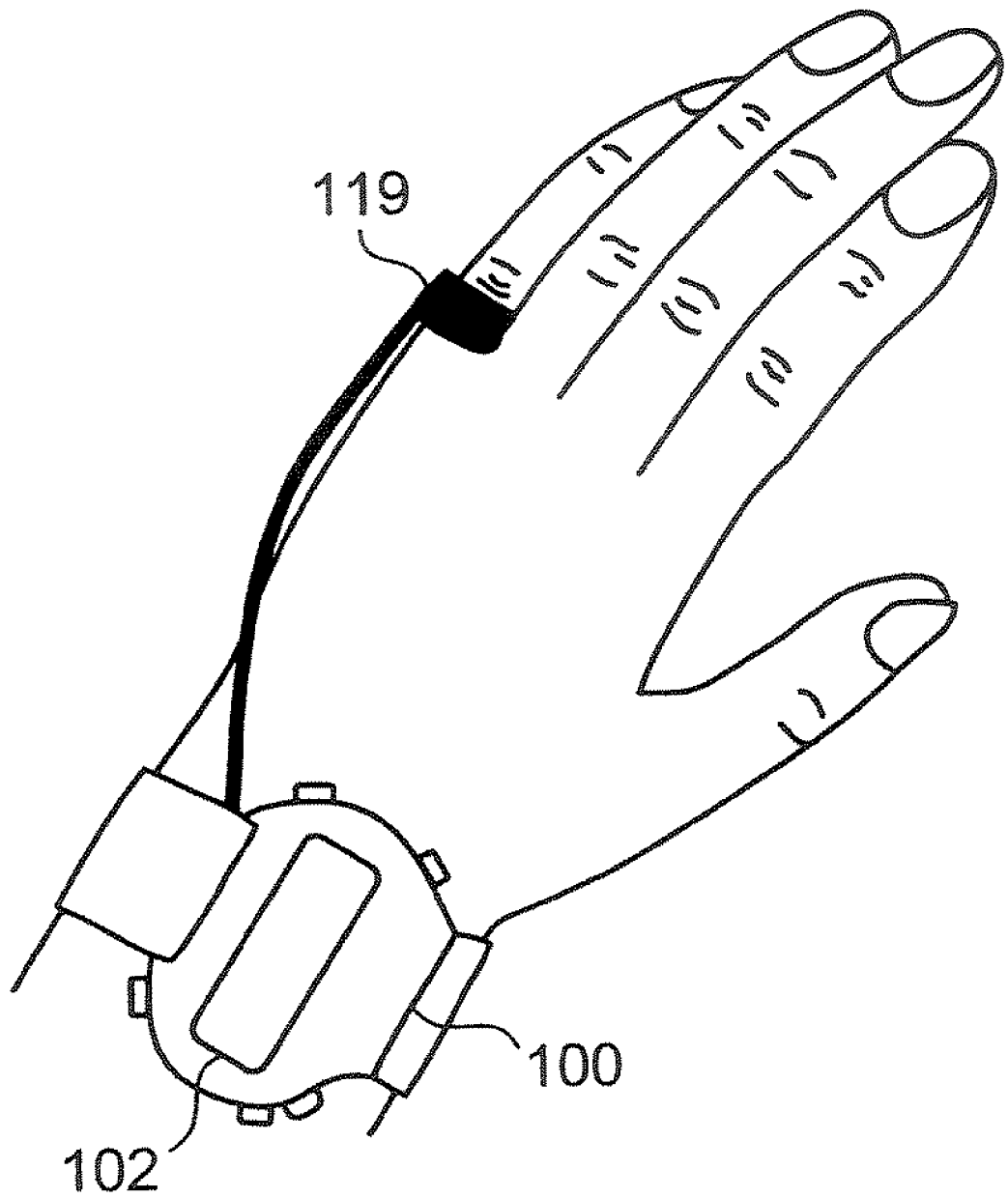
FIG. 2 is a diagram illustrating one example in which the sleep state measuring apparatus according to the first embodiment is mounted.

Here, an example of mounting the sleep state measuring apparatus 100, shown in FIG. 1, will be described. FIG. 2 is a diagram illustrating one example in which the sleep state measuring apparatus 100, shown in FIG. 1, is mounted. In FIG. 2, a pulse wave sensor 119 is mounted on a finger, and a main body of the sleep state measuring apparatus 100 is mounted on a wrist like a wristwatch. The pulse wave sensor 119 may be mounted on the palm of the hand by a plaster. In addition, a sleep state being measured, indexes obtained as a result of the measurement and the like, are displayed on the display unit 102. The displaying methods will be described below.

Returning to FIG. 1, the control unit 120 controls the entire sleep state measuring apparatus 100. The control unit 120 controls processing requests with respect to respective processing units and the flow of data while receiving user' demands and instructions. Specifically, while receiving user' demands, the control unit 120 controls power ON/OFF, starting of a sleep state determining function, display of a sleep state determining result, and the like.

The input unit 101 is a switch which allows the user to turn power ON/OFF, or which is used to perform a demand or an instruction for changing the display. The display unit 102 is a display device that displays a result of sleep state measurement on a radar chart. In the embodiment, an LCD is used as the display unit 120, but the display unit 120 may be constituted of any one of all display means which are generally used. An example of a display screen will be described later.

The storing unit 103 stores measurement data such as pulse wave data and body movement data, data after process such as pulse interval data, and a threshold value for determining a sleep state. Further, the storing unit 103 stores data, which is obtained by analyzing the above data, such as falling asleep, sleep time, sleep efficiency, healing degree, a sleeping rhythm index, body movement, arousal during sleep, and the like. The storing unit 103 correlates and maintains the above-mentioned indexes each other and can provide the maintained indexes with the user. Therefore, it is possible for the user to determine a sleep state in a multilateral manner based on the respective indexes.

Further, in the embodiment, a flash memory is used as the storing unit 103, but may be constituted of any one of all storing means which are generally used, for example, a HDD (Hard Disk Drive), a memory card, or the like. In addition, detailed descriptions of the falling asleep, sleep time, sleep efficiency, healing degree, sleeping rhythm index, body movement, and arousal during sleep will be made later.

The body movement measuring unit 104 measures acceleration data as body movement data indicating subject's body movement, and performs data conversion. The body movement measuring unit 104 is connected to the acceleration sensor 105. The acceleration sensor 105 is an accelerometer that measures the acceleration of −2G to 2G in each direction of three axes, and is provided inside the sleep state measuring apparatus 100. In addition, the body movement measuring unit 104 performs gain and offset controls of analog data of the acceleration sensor 105 in a control circuit, converts the analog data into a digital quantity by a 10-bit A/D converter, and inputs the converted digital quantity to the control unit 120. Also, the body movement measuring unit 104 of the present embodiment performs measurement every 50 ms, for example.

The pulse wave measuring unit 106 measures subject's pulse wave data and performs data conversion. The pulse wave measuring unit 106 includes the pulse wave sensor 119. The pulse wave sensor 119, which is formed of a blue LED and a photodiode, measures a pulse wave by irradiating light onto the surface of the finger skin and detecting fluctuation in reflected light, which changes according to the change in the bloodstream of a capillary vessel, by the photodiode. In addition, the pulse wave measuring unit 106 converts an output current from the photodiode of the pulse wave sensor 119 into a voltage by a current-to-voltage converter, amplifies the voltage by an amplifier, applies a high-pass filter (cutoff frequency=0.1 Hz) and a low-pass filter (cutoff frequency=50 Hz), performs conversion to a digital quantity by a 10-bit A/D converter, and inputs the converted digital quantity to the control unit 120.

The data communication unit 107 performs reception and transmission of data to/from personal computers and PDA terminals by wireless and the like. In addition, in the embodiment, the data communication unit 107 performs communication by using Bluetooth (registered trademark). However, the data communication unit 107 may perform communication using any one of all wire or wireless communication means generally used.

The time measuring unit 108 measures time. Specifically, a timer is used as the time measuring unit 108. In addition, the power supplying unit 109 is a power source which is supplied to the sleep state measuring unit 100. Specifically, a battery is used as the power supplying unit 109.

The body movement sampling data processing unit 111 obtains the amount of variation in body movement data and the amount of body movement, which is an average of the amount of variation in body movement within a pulse interval, based on the acceleration data in each direction of the three axes which is obtained by the body movement measuring unit 104.

Figure 3:
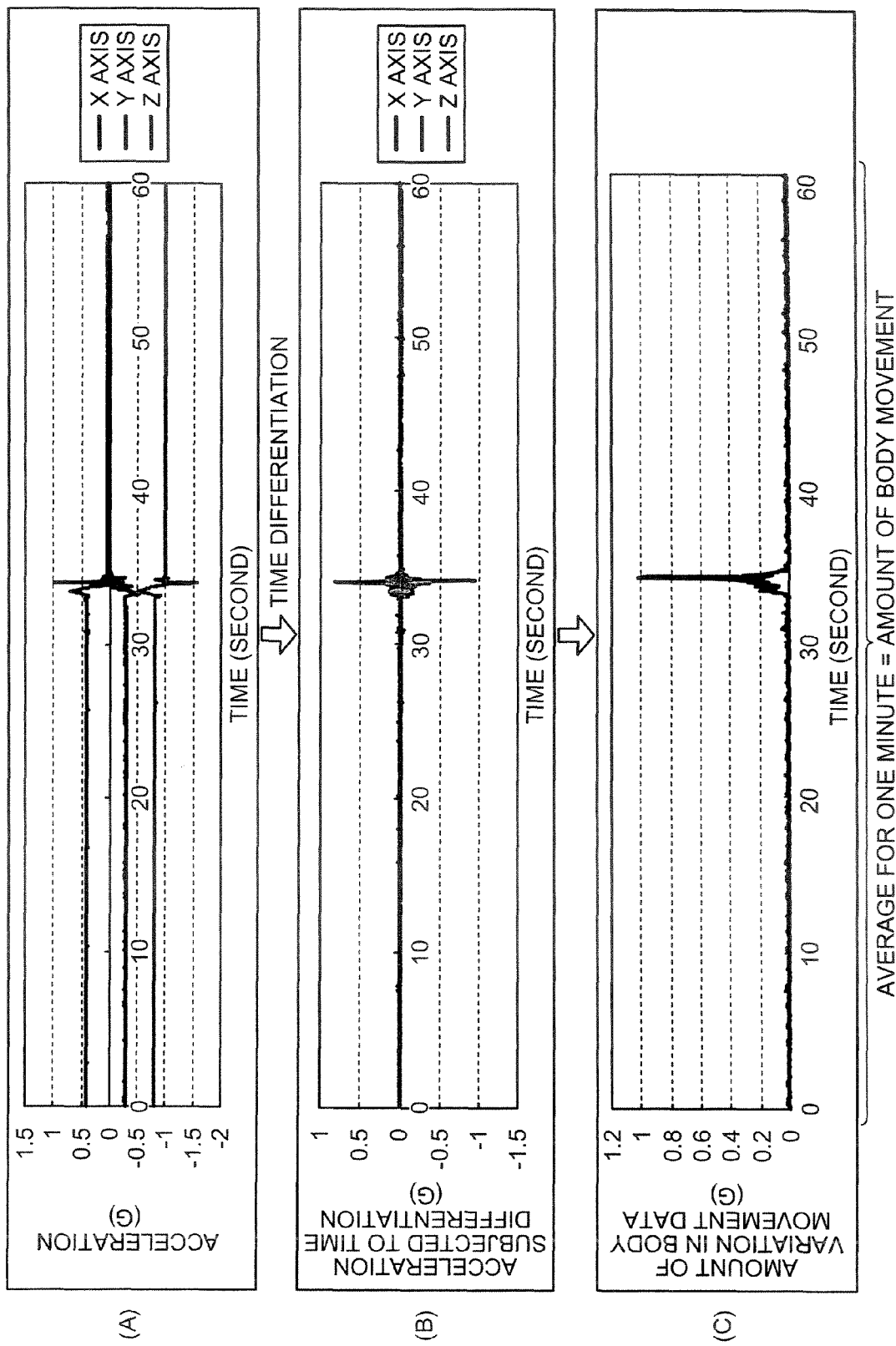
FIG. 3 is a view illustrating the procedure in which a body movement sampling data processing unit according to the first embodiment calculates the amount of variation in body movement data and the amount of body movement.

FIG. 3 is a view illustrating the procedure in which the body movement sampling data processing unit 111 calculates the amount of variation in body movement data and the amount of body movement. A graph shown in (A) of FIG. 3 exhibits an acceleration data in each direction of three axes, which is obtained from the body movement measuring unit 104. The body movement sampling data processing unit 111 performs time differentiation with respect to each obtained acceleration data, and calculates differential coefficients of the acceleration in each direction of the three axes. Changes for one minute of the calculated differential coefficients of the acceleration in each direction of the three axes are shown in (B) of FIG. 3. Next, the body movement sampling data processing unit 111 calculates the square root of the total sum of squares of the differential coefficients of the acceleration in each direction of the three axes. The calculated square root is designated as the amount of variation in body movement data. The changes for one minute in body movement data is shown in (C) of FIG. 3. Further, the body movement sampling data processing unit 111 calculates the amount of body movement, which is an average of the amount of variation in body movement data within a pulse interval, based on the calculated amount of variation in the body movement data. In addition, the amount of variation in body movement data in the present embodiment is designated as the amount of variation every 50 ms of user's body movement measured by the body movement measuring unit 104, for example. Furthermore, the amount of body movement is referred to an average value of the obtained amount of variation of the body movement data for one minute. The body movement sampling data processing unit 111 provides the amount of variation in body movement data and the amount of body movement to the body movement determining unit 151 as data for determining the body movement.

Returning to FIG. 1, the awakening/sleeping determining unit 110 determines whether the subject is awakened or not based on the subject's body movement data, and includes the body movement determining unit 151 and the awakening determining unit 152. The body movement determining unit 151 determines body movement of the user having the sleep state measuring apparatus 100. In addition, the awakening determining unit 152 determines whether the user is sleeping or awake based on the occurrence frequency of body movement, which is determined by the body movement determining unit 151.

Figure 4:
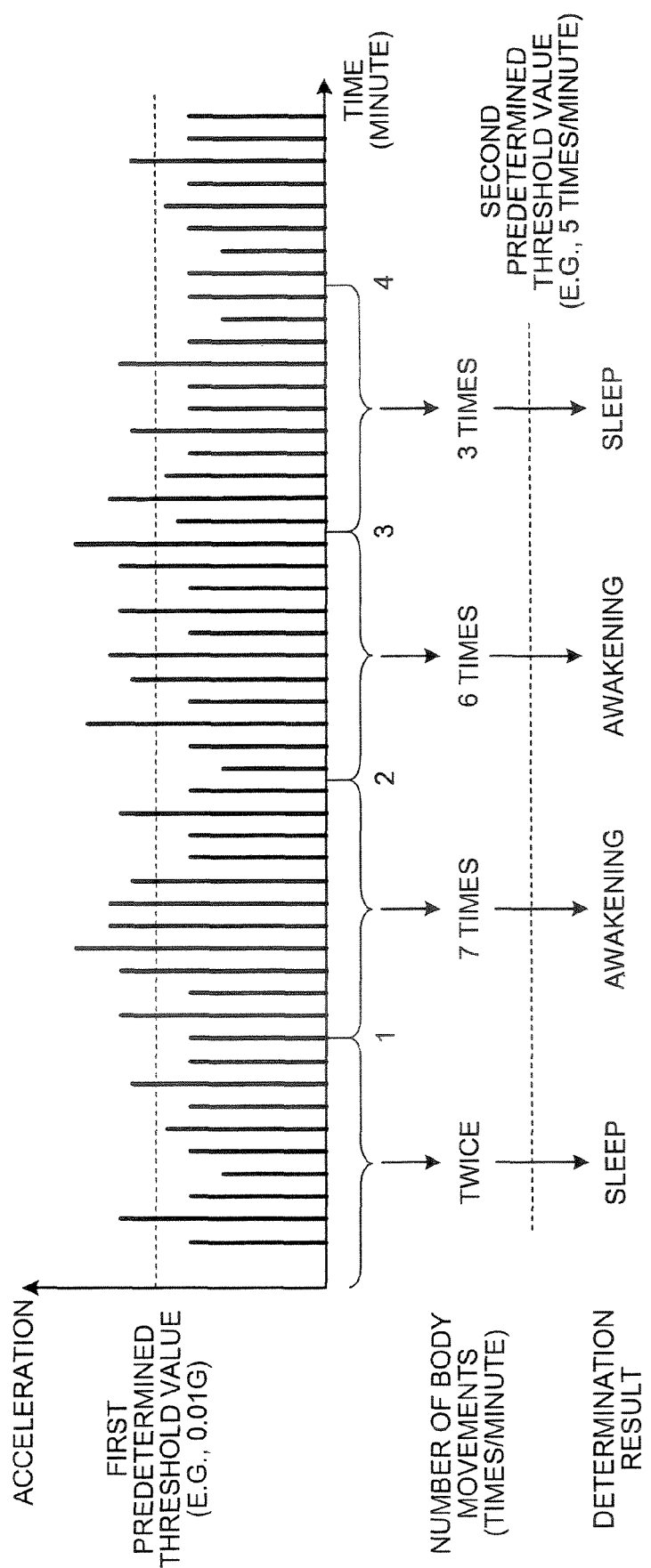
FIG. 4 is a view illustrating an example in which an awakening/sleeping determining unit determines whether a user is sleeping or not.

FIG. 4 is a view illustrating an example in which the awakening/sleeping determining unit 110 of the sleep state measuring apparatus 100 determines whether the user is sleeping or not. For the purpose of simplicity, a second predetermined threshold value corresponds to 5 times/min, for example. A first predetermined threshold value uses 0.01G, which is the minimum value for a very small amount of body movement which is used in a body movement meter. The body movement determining unit 151 compares whether the amount of variation in the body movement data, obtained from the body movement sampling data processing unit 111, is equal to or greater than the first determined threshold value, and determines that the user has moved the body if the amount of variation exceeds the first predetermined threshold value.

The awakening determining 152 obtains from the body movement determining unit 151 whether or not there is the body movement, and measures the occurrence frequency of body movement during a setting interval. Here, it is preferable that the setting interval corresponds to one minute. In the embodiment, the awakening determining unit 152 determines that the user is in an awakening state when the frequency of the body movement occurring is equal to or greater than the second predetermined value. On the other hand, the awakening determining unit 152 determines that the user is in a sleep state when the frequency of the body movement occurring is less than the second predetermined value.

In addition, in another example other than the present embodiment, the awakening determining unit 152 may determine that the user is in an awakening state when the frequency of the body movement occurring, which is determined by the body movement determining unit 151, is equal to or greater than the second predetermined threshold value, and at the same time, pulse interval data to be obtained during a process to be described later is shorter than an average value of pulse interval data during sleep in the past. In addition, preferably, the second predetermined threshold value corresponds to 20 times/min based on the frequency of the body movement occurring when the user was awakened in the past.

Returning to FIG. 1, the pulse wave sampling data processing unit 112 samples pulse wave data from a pulse wave of the user having the sleep state measuring apparatus 100 mounted thereon so as to obtain pulse interval data.

Specifically, the pulse wave sampling data processing unit 112 samples pulse wave data from a pulse wave, performs time differentiation for a series of sampled pulse wave data so as to remove the direct current variation component from the series of pulse wave data. In addition, the pulse wave sampling data processing unit 112 obtains the maximum value and the minimum value of the pulse wave data for about one second before and after the series of a processing point of the pulse wave data from which the direct current variation component is removed. Further, the pulse wave sampling data processing unit 112 sets a predetermined value between the maximum value and the minimum value as a third predetermined value. For example, the pulse wave sampling data processing unit 112 sets a difference between the maximum value and the minimum value as the amplitude, and uses a value of 90 percent of the amplitude from the minimum value as the third predetermined threshold value. In addition, the pulse wave sampling data processing unit 112 calculates the time when the value of the series of pulse wave data, which corresponds to the third predetermined value, is generated from the pulse wave data from which the direct current variation component is removed. Further, the pulse wave data processing unit 112 obtains pulse interval data based on an interval of the calculated time.

The pulse interval data processing unit 113 generates a series of pulse interval data from the pulse interval data obtained by the pulse wave sampling data processing 112, for example, a data set for one minute, and interpolates the series of pulse interval data by a polynomial of higher degree. Here, one example is described, in which the pulse interval data processing unit 113 interpolates the series of pulse interval data.

Figure 5:
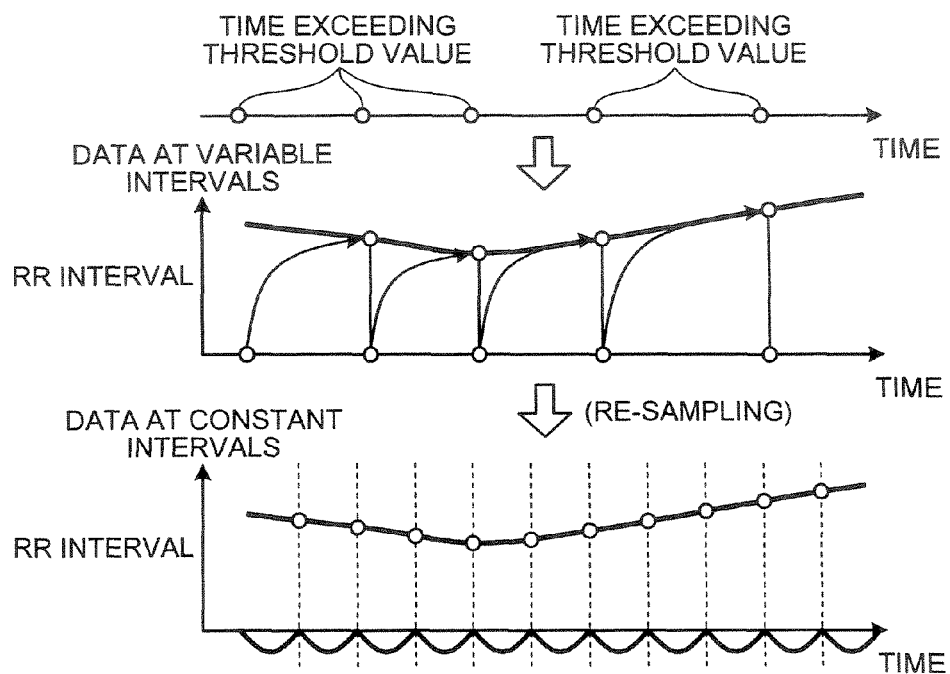
FIG. 5 is a view illustrating one example in which a pulse interval data processing unit according to the first embodiment interpolates a series of pulse interval data.

FIG. 5 is a view illustrating one example in which the pulse interval data processing unit 113 interpolates a series of pulse interval data. As shown therein, the pulse interval data processing unit 113 interpolates pulse interval data at variable intervals, re-samples the interpolated pulse interval data, and generates pulse interval data at constant intervals. For example, in an interpolation method, the pulse interval data processing unit 113 generates pulse interval data at constant intervals by using respective three sampling points, that is, a point for interpolation and a point before and after the point for interpolation, according to a tertiary polynomial interpolation. Therefore, the pulse interval data processing unit 113 generates pulse interval data at constant intervals from the series of pulse interval data at variable intervals. Accordingly, it is possible for the autonomic nerve index data processing unit 114 to convert the generated pulse interval data at constant intervals into frequency spectrum distribution.

The autonomic nerve index data processing unit 114 includes a frequency spectrum converting unit 161 and an autonomic nerve index obtaining unit 162, and obtains two autonomic nerve indexes, that is, an index LF of a low-frequency area (around 0.05 to 0.15 Hz) and an index HF of a high-frequency area (around 0.15 to 0.4 Hz) so as to determine a sleep state. The frequency spectrum converting unit 161 converts the series of pulse interval data, processed by the pulse interval data processing unit 113, into frequency spectrum distribution according to an analysis method such as a Fast Fourier Transform (FFT). In addition, the autonomic nerve index obtaining unit 162 obtains autonomic nerve indexes LF and HF from a plurality of power spectrum values of the series of pulse interval data which is converted into frequency spectrum distribution by the frequency spectrum converting unit 161. Specifically, the autonomic nerve index obtaining unit 162 obtains LF and HF, each of which is an arithmetical average of the total value of three points, that is, a peak value of each of the multiple power spectrums, and a point before and after the peak value.

Figure 6:
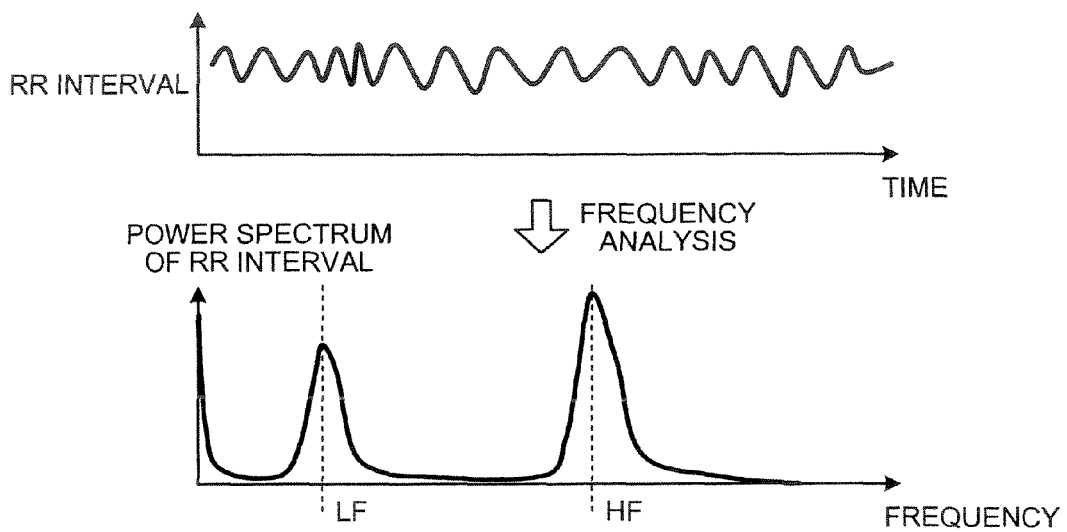
FIG. 6 is a view illustrating one example in which an autonomic nerve index data processing unit according to the first embodiment obtains autonomic nerve indexes LF and HF from values of power spectrums.

Here, an example will be described, in which the autonomic nerve index data processing unit 114 obtains autonomic nerve indexes LF and HF from values of power spectrums. FIG. 6 is a view illustrating one example in which the autonomic nerve index data processing unit 114 obtains autonomic nerve indexes LF and HF from values of power spectrums. When the pulse interval data processing unit 113 generates pulse interval data at constant intervals, the autonomic nerve index data processing unit 114 performs frequency analysis so as to convert the series of pulse interval data into frequency spectrum distribution. In addition, a frequency analysis method may include any one of AR-model, a maximum entropy method, a wavelet method, and the like. In the present embodiment, however, the autonomic nerve index data processing unit 114 uses a fast fourier transform (FFT) that allows small loads when processing data.

The sleep state measuring apparatus 100 calculates indexes used to recognize a user's sleep state based on the above-described data. The calculated indexes include seven indexes, that is, falling asleep, sleep time, sleep efficiency, healing degree, a sleeping rhythm index, body movement, and arousal during sleep.

The falling asleep detecting unit 121 obtains user's falling asleep. The falling asleep corresponds to a reciprocal number of sleep onset latency (time from bedtime to sleep onset time). The bedtime corresponds to the time that the user instructs the sleep state measuring apparatus 10 to start measurement or the time that the user inputs an instruction to the input unit 101 that the user went to bed. In the configuration included in the sleep state measuring apparatus 100, it may be determined whether the user went to bed or not according to an angle of a user's wrist, which is obtained from the acceleration sensor 105. For example, when the frequency of the detected angle of the wrist, which becomes around an angle of an arm in the supine position, is higher than a predetermined frequency, it may be determined that the user went to bed. The sleep onset time is designated as the time that the awakening/sleeping determining unit 110 determines sleep for the first time after bedtime.

The sleep time obtaining unit 116 obtains sleep time of the user mounting the sleep state measuring apparatus 100. The sleep time is a difference between awakening time and sleep onset time. The awakening time is the time that the awakening/sleeping determining unit 110 determines when the user changes from sleep to awakening just before finishing measurement.

The sleep efficiency obtaining unit 117 obtains sleep efficiency of the user mounting the sleep state measuring apparatus 100 thereon. The sleep efficiency is designated as a ratio of time, from which awakening is excluded, within sleep time. For example, the sleep efficiency obtaining unit 117 calculates sleep efficiency by dividing the time determined as sleeping by the awakening/sleeping determining unit 110 by the sleep time obtained by the sleep time obtaining unit 116.

The sleep state determining unit 122 determines the user's sleep state based on the values of LF and HF obtained by the autonomic nerve index data processing unit 114. Specifically, the sleep state determining unit 122 determines that the user's sleep state corresponds to deep sleep when the value of LF/HF is less than a first determination threshold value and at the same time, the value HF is equal to or greater than a second determination threshold value. In addition, the sleep state determining unit 122 determines that the user's sleep state corresponds to REM sleep when the value of LF/HF is equal to or greater than a third determination threshold value, the value HF is less than a fourth determination threshold value, and at the same time, the total sum of the standard deviations of the values LF and HF is equal to or greater than a fifth determination threshold value. Furthermore, the sleep state determining unit 122 determines that the user's sleep state is shallow sleep other than when the user's sleep state corresponds to deep sleep or REM sleep.

The healing degree calculating unit 118 includes a comparing unit 181, a difference normalizing unit 182 and an average obtaining unit 183, and calculates user's healing degree (an index of parasympathetic nerve dominance). The comparing unit 181 compares whether HF is greater than LF or not. In addition, HF and LF are values obtained by the autonomic nerve index data processing unit 114. When the comparing unit 181 determines that HF is greater than LF, the difference normalizing unit 182 calculates a difference between HF and LF and divides the calculated difference by the HF so as to normalize the divided difference. The normalized value becomes the healing degree. The average obtaining unit 183 calculates an average value of the healing degree during sleep based on the healing degree which is obtained every predetermined time by the difference normalizing unit 182.

Figure 7:
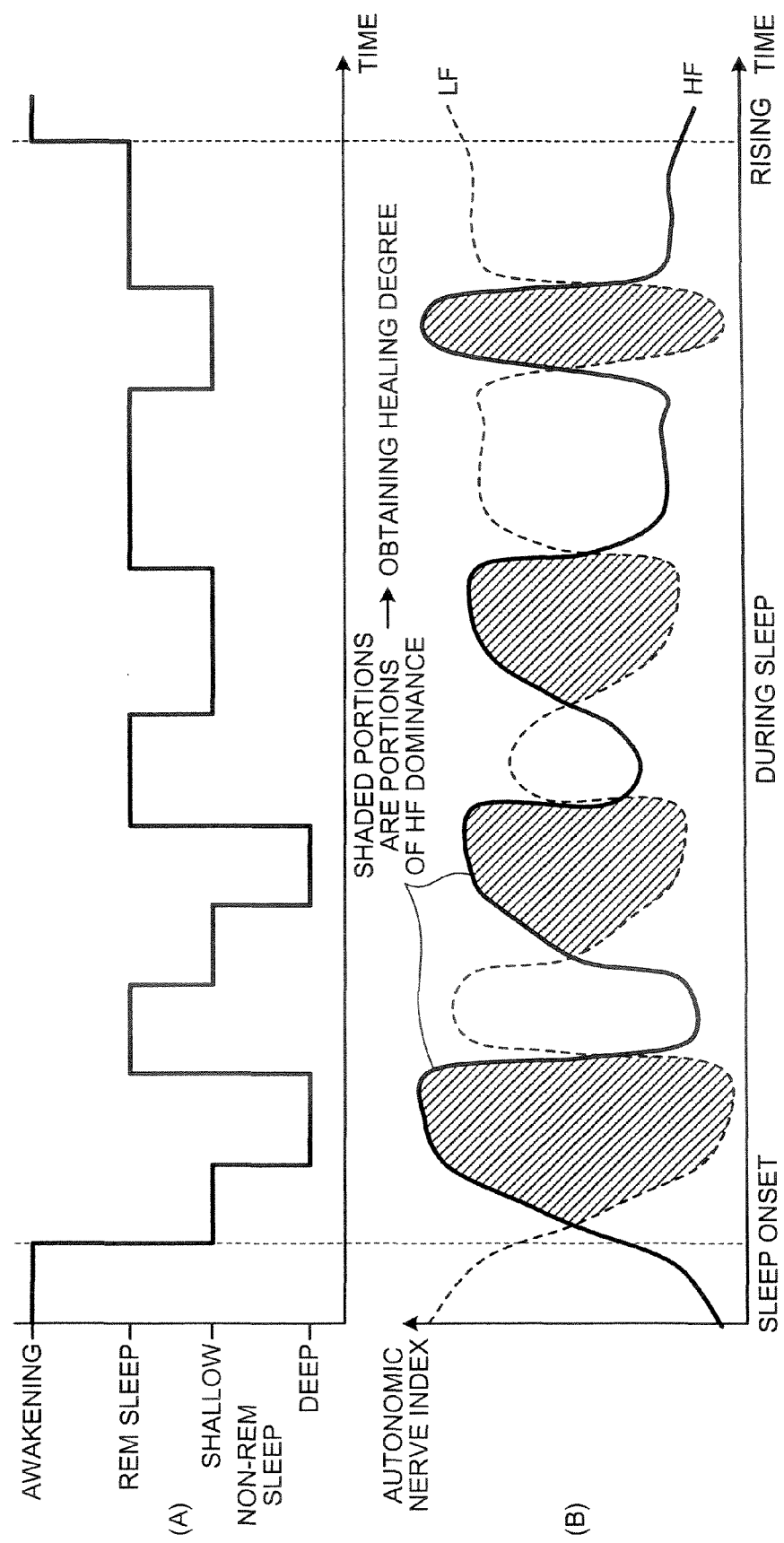
FIG. 7 is a view showing the concept in which a healing degree calculating unit according to the first embodiment calculates healing degree.

FIG. 7 is a view showing the concept in which the healing degree calculating unit 118 calculates healing degree. In (A) of FIG. 7, changes of the sleep state determined by the sleep state determining unit 122 are shown. In addition, in (B) of FIG. 7, changes of HF and LF obtained by the autonomic nerve index data processing unit 114 are shown. It is possible to obtain healing degree based on shaded portions shown in (B) of FIG. 7, that is, based on the time that HF has priority over LF.

In addition, it is possible to understand the relationship between the healing degree and the sleep state by comparing (A) and (B) in FIG. 7. Specifically, as shown in (A) and (B) in FIG. 7, at the time that the user's sleep state corresponds to a deep-sleep state in a sleep state cycle, HF becomes greater than LF and the healing degree calculating unit 118 obtains healing degree.

Here, the healing degree means a degree of parasympathetic nerve dominance. For example, the healing degree shows a low value when it is hard to fall asleep and a sleep state corresponds to shallow sleep, and a high value when a sleep state corresponds to deep sleep. That is, it is possible for the user to detect a degree in which the user feels comfortable during sleep. In other words, the healing degree is an index by which sleep quality can be detected.

The sleeping rhythm index data processing unit 115 includes a sleeping rhythm obtaining unit 171 and calculates a sleeping rhythm index based on the changes of HF obtained by the autonomic nerve index data processing unit 114. The sleeping rhythm obtaining unit 171 calculates changes of HF, which are ideal for each of the users, based on the changes of HF obtained by the autonomic nerve index data processing unit 114. Here, the ideal change of HF is assumed to be the change of a user's sleeping cycle. The sleeping rhythm index data processing unit 115 obtains a sleeping rhythm index based on the changes of HF obtained by the autonomic nerve index data processing unit 114, and the changes of the user's sleeping cycle obtained by the sleeping rhythm obtaining unit 171.

Figure 8:
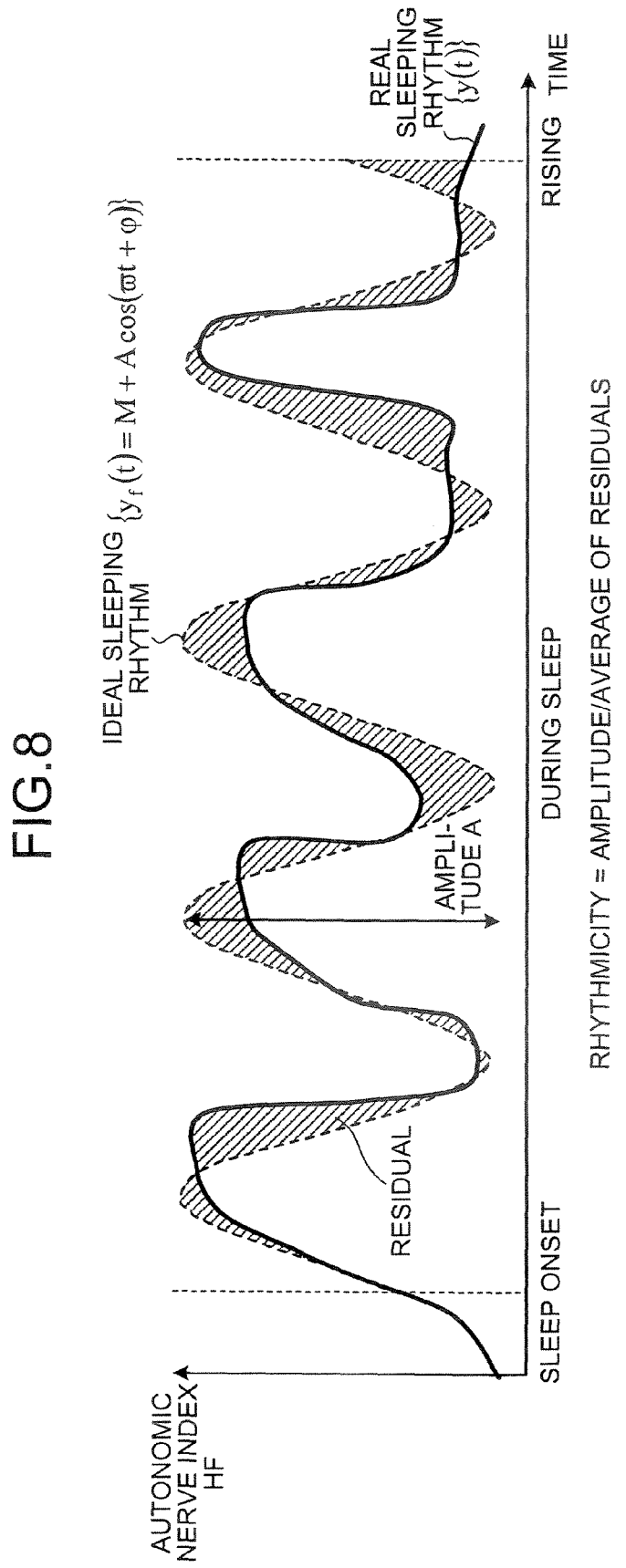
FIG. 8 is a view illustrating the concept in which a sleeping rhythm index data processing unit according to the first embodiment calculates a sleeping rhythm index.

FIG. 8 is a view illustrating the concept in which the sleeping rhythm index data processing unit 115 calculates a sleeping rhythm index. As shown therein, real changes of HF obtained by the sleeping rhythm index data processing unit 115, and user's ideal changes of HF, that is, changes of a sleeping cycle are shown. The sleeping rhythm index data processing unit 115 calculates an average of residuals between the real changes of HF and the ideal changes of HF, which are shown as shaded portions. Here, a value obtained by dividing the amplitude of the ideal changes of HF by the calculated average of residuals becomes a sleeping rhythm index. Here a sleeping rhythm index corresponds to a sleep periodicity index. a sleep periodicity index indicates whether a user is sleeping or not according to a user's ideal sleeping cycle as an index. Now, a method of calculating the ideal changes of HF will be described.

The sleeping rhythm obtaining unit 171 calculates ideal changes of HF according to the time lapse based on time lapse of HF obtained by the autonomic nerve index data processing unit 114. In the embodiment, the sleeping rhythm obtaining unit 171 obtains ideal changes of HF for each of the users by least-squares fitting of a moving average of HF to a cosine wave, for example. Further, the changes of HF in conjunction with time lapse, which are really obtained by the autonomic nerve index data processing unit 114, are designated as y(t). In addition, a time function $y_f(t)$ of HF, in which time square fitting has been performed, to be obtained by the sleeping rhythm obtaining unit 171 is expressed in Equation (1).

$$y_f(t)=M+A\cos(\omega t+\omega) \quad (1)$$

In addition, a sleeping rhythm of a human being has an approximate 90-minute repeating cycle. For this reason, the sleeping rhythm obtaining unit 171 designates ω as a value between 60 minutes and 120 minutes, for example. In addition, the sleeping rhythm obtaining unit 171 calculates values of M, A and f according to a method of least squares. Thereafter, the sleep rhythm obtaining unit 171 obtains the value ω, which allows the minimum residual. According to such procedure, it is possible for the sleeping rhythm obtaining unit 171 to obtain the ideal changes of HF for each of the users. Meanwhile, the method of calculating time lapse of HF is not limited to the above-described procedure. For example, least square fitting may be performed using a sine wave.

Furthermore, the sleeping rhythm index data processing unit 115 divides the amplitude A obtained by the sleeping rhythm obtaining unit 171 by the square root average of the residual sum of squares in y(t) and y$_f$(t) so as to calculate a sleeping rhythm index. An equation for obtaining the sleeping rhythm index r is expressed in Equation (2).

$$r = A \bigg/ \sum_{i=1}^{n} \left(\sqrt{\{y(t_i) - y_f(t_i)\}^2} \bigg/ n\right) \qquad (2)$$

Here, $t_i$ in Equation (2) refers to the time that the autonomic nerve index data processing unit 114 obtains HF.

The larger the amplitude is and the smaller an error is, the greater value the sleeping rhythm index to be calculated in Equation (2) has. Namely, the more the really obtained HF corresponds to the time function obtained by the sleeping rhythm obtaining unit 171, the greater value the sleeping rhythm index has. Therefore, the greater the sleeping rhythm index is, the more adequate rhythm the user's sleep follows. Accordingly, referring to the sleeping rhythm index, the user can determine whether the sleep state is changed into an adequate rhythm during sleep. In other words, same as the healing degree, the sleeping rhythm index becomes an index used to detect sleep quality.

The body movement amount obtaining unit 123 obtains an average amount of body movement during sleep based on body movement measured by the body movement measuring unit 104. The arousal during sleep obtaining unit 124 obtains the number and the total time of arousal during sleep based on a determination result of the awakening/sleeping determining unit 110. Here, the arousal during sleep refers to awakening from sleep onset to rising, and includes momentary awakening. In addition, in the embodiment, the arousal during sleep obtaining unit 124 obtains the number and the total time of awakenings after sleep onset. However, any one of the number and the total time of awakenings after sleep onset may be obtained as a value showing arousal during sleep. Further, a result of the determination of the awakening/sleeping determining unit 110 may be previously stored in the storing unit 103.

The values obtained by the above-described configuration are stored in the storing unit 103. FIG. 9 is a view illustrating an example of indexes indicating a sleep state, which can be obtained by the sleep state measuring apparatus 100 that measures overnight sleeping of a user A. In addition, even though sleep onset latency is shown in FIG. 9, it is possible to obtain falling asleep by calculating a reciprocal number of the sleep onset latency. Though not shown in the drawing, it is also possible to obtain a sleep state which is determined by the sleep state determining unit 122 and changes together with time lapse.

Returning to FIG. 1, when displaying the measurement result, the deviation value obtaining unit 125 obtains a deviation value for each of indexes of the user whose sleep is measured. For this reason, the storing unit 103 previously stores sleep time, sleep efficiency, healing degree, body movement, rhythmicity, falling asleep (a reciprocal number of sleep onset latency), and arousal during sleep, which are obtained from multiple users. Therefore, when the measurement result of the user A whose sleep is measured is displayed, the deviation value obtaining unit 125 calculates a deviation vale of the user A based on an average value and a deviation value of the indexes of the multiple users, which are previously stored in the storing unit 103. In addition, the body movement and the arousal during sleep show a better sleep state when they have lower values. Here, for each of the body movement and the arousal during sleep, a reciprocal number is obtained, and then a deviation value is calculated based on the reciprocal number. Accordingly, the greater values the indexes have, the better sleep state the indexes indicate.

Figure 10:
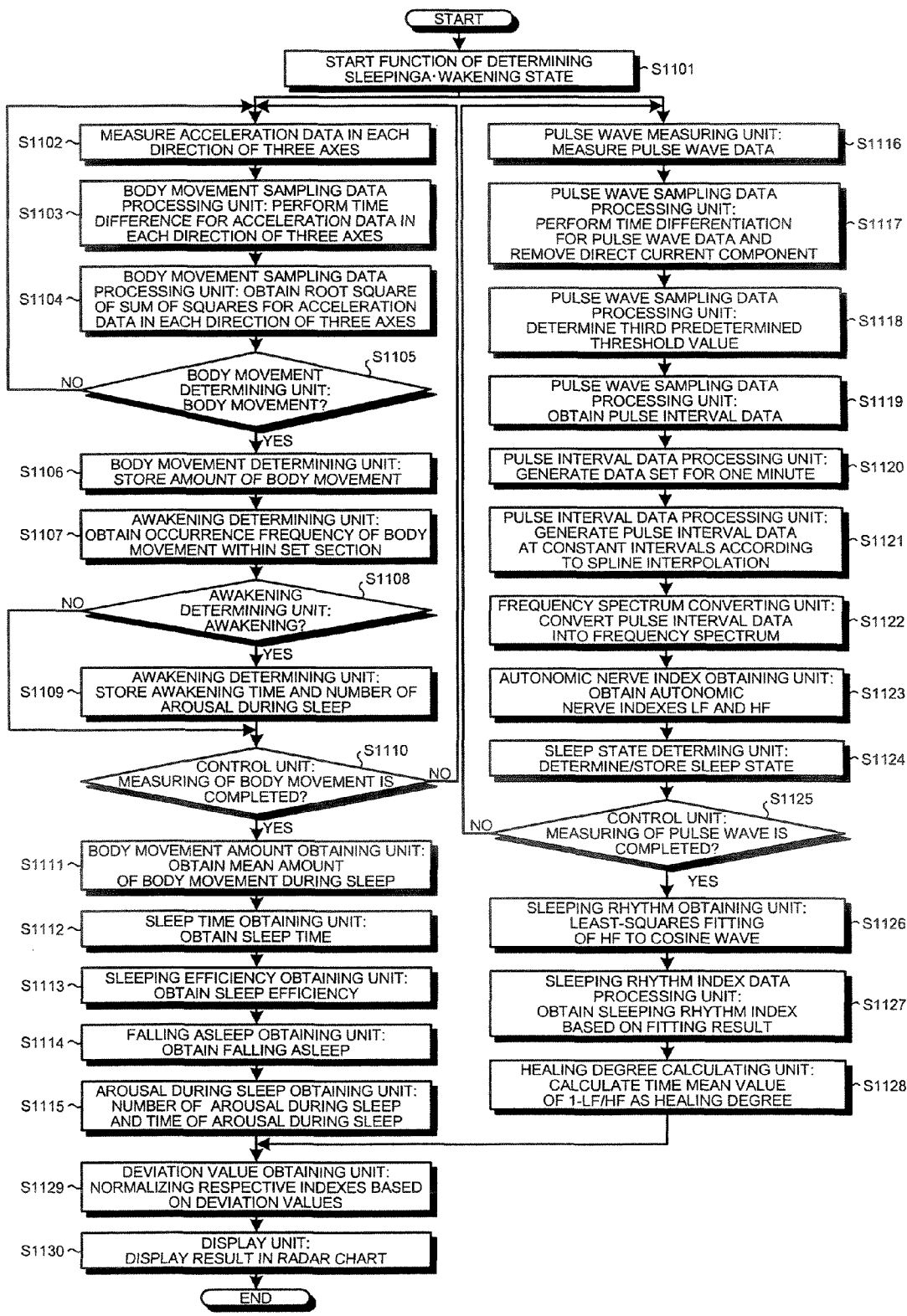
FIG. 10 is a flowchart illustrating the sleep state measuring procedure in the sleep state measuring apparatus.

In the sleep state measuring apparatus 100, the procedure in which a sleep state is measured while the control unit 120 controls each of the units will be described. FIG. 10 is a flowchart illustrating the sleep state measuring procedure performed in the sleep state measuring apparatus 100.

First, the sleep state measuring apparatus 100 is mounted to the user. When the input unit 101 receives an input from the user, the control unit 150 starts power and a sleep state measuring function (Step S1101). Next, the body movement measuring unit 104 starts to measure acceleration data by the acceleration sensor 105, and the pulse wave measuring unit 106 starts to measure pulse wave data by the pulse wave sensor 119 (Steps S1102 and S1116).

The body movement sampling data processing unit 111 performs time differentiation for the acceleration data in each direction of three axes, obtained from the body movement measuring data 104, so as to calculate differential coefficients of the acceleration in each direction of the three axes (Step S1103). Further, the body movement sampling data processing unit 111 calculates the square root of the sum of squares for the respective differential coefficients in each direction of the three axes (Step S1104).

The body movement determining unit 151 obtains the square root of the sum of squares for the differential coefficients in each direction of the three axes, which is calculated by the body movement sampling data processing unit 111, and determines based on the obtained value whether it is body movement or not (Step S1105). Specifically, the body movement determining unit 151 determines that it is body movement when the amount of variation in body movement is equal to or greater than a first predetermined threshold value. Here, the amount of variation in body movement is the square root of the sum of squares for the differential coefficients in each direction of the three axes, which is calculated by the body movement sampling data processing unit 111. For example, 0.01G, which is the minimum value for a very small amount of body movement used in a body movement meter, is used for the first predetermined threshold value. When the body movement determining unit 151 determines that it is not body movement (Step S1105: NO), the process is performed again from measurement of the body movement measuring unit 104 (Step S1102).

When the body movement determining unit 151 determines that there is body movement (Step S1105: YES), the body movement determining unit 151 maintains the amount of body movement in the storing unit 103 (Step S1106).

The awakening determining unit 152 obtains an occurrence frequency of body movement during a setting interval, for example one minute (Step S1107). The awakening determining unit 152 determines whether it is awakening or not based on the obtained occurrence frequency of body movement within the setting interval (Step S1108). Specifically, the awakening determining unit 152 determines that the user is awakened when the occurrence frequency of body movement, determined by the body movement determining unit 151, is equal to or greater than a second predetermined threshold value. The awakening determining unit 152 determines that the user is during sleep when the occurrence frequency of body movement is less than the second predetermined threshold value. For example, the second predetermined threshold value corresponds to 20 times/minute based on the occurrence frequency of body movement at the time of awakening in the past.

As a result, when the awakening determining unit 152 determines that the user is awakened (Step S1108: YES), the awakening determining unit 152 stores the awakening time and the number of arousal during sleep in the storing unit 103 (Step S1109). Alternatively, when the awakening determining unit 152 determines that the user is not awakened (Step S1108: NO), a particular process is not performed in general. However, when the awakening determining unit 152 determines that the user is not awakened this time but awakened last time, the awakening determining unit 152 determines that the user is at sleep onset and stores sleep onset time in the storing unit 103. Next, the control unit 120 determines whether the measurement of body movement is completed or not according to the user's input from the input unit 101 (Step S1110). In addition, when the control unit 120 determines that the measurement of body movement is not completed (Step S1110: NO), the process is performed again from measurement of the body movement measuring unit 104 (Step S1102).

Alternatively, when the control unit 120 determines that the measurement of body movement is completed (Step S1110: YES), the body movement amount obtaining unit 123 obtains the average amount of body movement during sleep based on the body movement which is measured by the body movement measuring unit 104 and is previously stored in the storing unit 103 (Step S1111). Then, the sleep time obtaining unit 116 obtains sleep time based on the difference between the awakening time and the sleep onset time which are stored in the storing unit 103 (Step S1112). Next, the sleep efficiency obtaining unit 117 obtains sleep efficiency based on a ratio of time other than the awakening time within the sleep time (Step S1113).

Next, the falling asleep obtaining unit 121 obtains falling asleep based on a reciprocal number of sleep onset latency (the time from bedtime to sleep onset time) (Step S1114). The arousal during sleep obtaining unit 124 obtains the number and the total time of arousal during sleep based on the number of arousal during sleep stored in the storing unit 103, and time of arousal during sleep generated during halfway (differential time between awakening time and sleep onset time) (Step S1115).

The pulse wave sampling data processing unit 112 samples pulse wave data from a pulse wave and performs time differentiation for a series of sampled pulse wave data, thereby obtaining a direct current variation component of the series of pulse wave data, and removes the variable direct current component from the series of pulse wave data (Step S1117). The pulse wave sampling data processing unit 112 obtains the minimum value and the maximum value of the pulse wave data within a predetermined period of time from the series of pulse wave data from which the variable direct current component is removed. Further, the pulse wave sampling data processing unit 112 determines a predetermined value between the maximum value and the minimum value as a third predetermined threshold value (Step S1118). For example, when the difference between the maximum value and the minimum value is adopted as an amplitude, a value corresponding to ninety percent of the amplitude from the minimum value is used as the third predetermined threshold value. In addition, the pulse wave sampling data processing unit 112 calculates the time that the value of the series of pulse wave data, which corresponds to the third predetermined threshold value, is found, and obtains pulse interval data based on an interval of the calculated time (Step S1119).

The pulse interval data processing unit 113 generates a data set for one minute using a series of pulse interval data (Step S1120). Further, the pulse interval data processing unit 113 interpolates the series of pulse interval data according to spline interpolation, that is, by a polynomial of higher degree so as to generate pulse interval data having constant intervals (Step S1121).

The frequency spectrum converting unit 161 converts the series of pulse interval data, processed by the pulse interval data processing unit 113, into frequency spectrum distribution according to a frequency analysis method such as a FFT method (Step S1122). The autonomic nerve index obtaining unit 162 obtains autonomic nerve indexes LF and HF based on values of multiple power spectrums of the series of pulse interval data converted into the frequency spectrum distribution by the frequency spectrum converting unit 161 (Step S1123). Specifically, the indexes LF and HF are obtained by calculating the arithmetic means of the sum of three points, that is, a peak value of each of the multiple spectrums and one point before and after the peak value. Here, one point before the peak value has the same interval as the other point after the peak value.

Next, the sleep state determining unit 122 determines a user's sleep state based on the obtained LF and HF, and the storing unit 103 stores a result of the determination (Step S1124). Meanwhile, criteria for determining a sleep state is described above, and thus a description thereof is not repeated.

Further, the control unit 120 determines whether the measuring of the pulse wave is completed or not based on the user's input from the input unit 101 and others (Step S1125). When the control unit 120 determines that the measurement of the pulse wave is not completed (Step S1125: NO), the process is performed again from measurement of the pulse wave measuring unit 106 (Step S1116).

When the control unit 120 determines that the measurement of the pulse wave is completed (Step S1125: YES), the sleeping rhythm obtaining unit 171 calculates ideal changes of HF according to time lapse for each of the users by least-squares fitting of the HF to a cosine wave (Step S1126).

Next, the sleeping rhythm index data processing unit 115 calculates a sleeping rhythm index based on a fitting result (Step S1127). Specifically, the sleeping rhythm index data processing unit 115 calculates a sleeping rhythm index by dividing the change of HF obtained by the autonomic nerve index data processing unit 114 by the square root average of the residual sum of squares in a time function of HF, which is the fitting result.

When the healing degree calculating unit 118 determines that HF is equal to or greater than LF, the healing degree calculating unit 118 calculates the time mean value of 1−LF/HF as healing degree (Step S1128).

The deviation value obtaining unit 125 obtains deviation values of the body movement, sleep time, sleep efficiency, falling asleep, number and time of arousal during sleep, sleeping rhythm index and healing degree, which are obtained according to the above-described steps of S1111 to S1115, S1127 and S1128 (Step S1129). Specifically, for example, the deviation value obtaining unit 125 calculates deviation values of the user mounting the sleep state measuring apparatus 100 thereon based on an average value and a standard deviation of each of the indexes of the multiple users, which are stored in the storing unit 103.

Then, the display unit 102 displays the deviation values of the respective indexes, which are obtained by the deviation value obtaining unit 125 (Step S1130).

Figure 11:
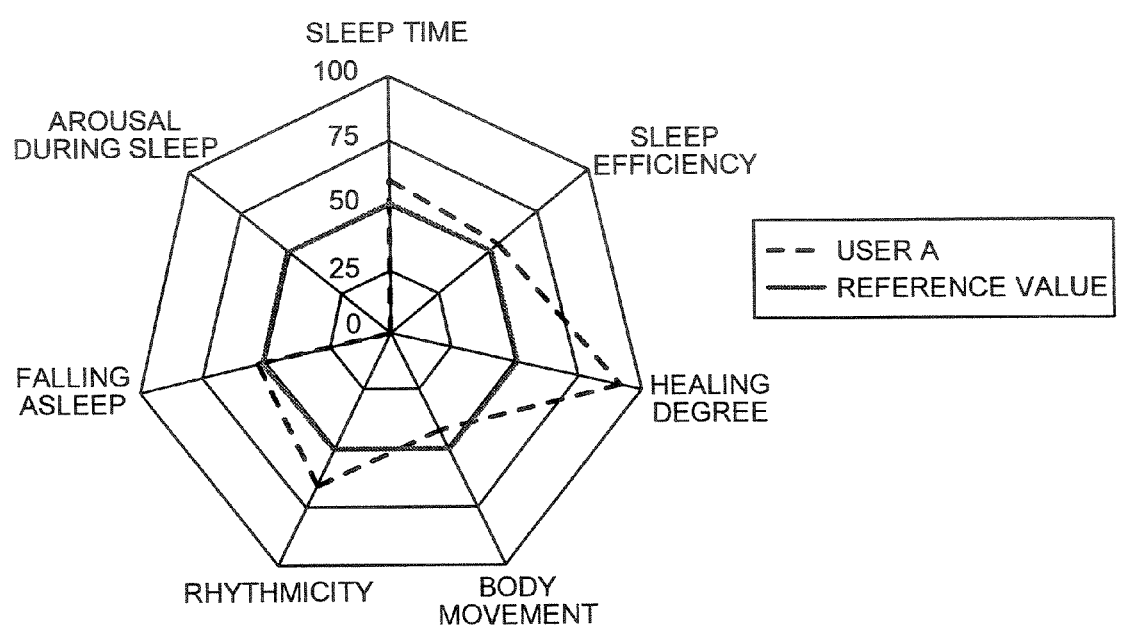
FIG. 11 is a view illustrating one example of a radar chart showing a measuring result of sleeping which is displayed by the display unit according to the first embodiment.

FIG. 11 is a view illustrating one example of a radar chart showing a measuring result of sleeping which the display unit 102 displays. As shown therein, the deviation values of the respective indexes, obtained by the deviation value obtaining unit 125, are displayed on the display unit 102. Therefore, it is possible for the user to understand his or her sleep state in detail as well as the sleep time and the like. In FIG. 11, an average value of the multiple users is shown as a criterion.

As described above, in a first embodiment, it is possible for the sleep state measuring apparatus 100 to show a user's sleep state in a multilateral manner by calculating a sleeping rhythm index and healing degree based on autonomic nerve indexes LF and HF, which are obtained at the same time by measurement, together with data about sleeping/awakening and body movement. Further, the sleep state measuring apparatus 100 displays multiple indexes, for example, in the form of a radar chart and the like when expressing the sleep state. Accordingly, it is possible for the sleep state measuring apparatus 100 to provide the multiple indexes to the user, who is able to easily recognize a sleep state.

According to the above-described embodiment, the sleep state measuring apparatus obtains indexes such as healing degree, a sleeping rhythm index, or the like. Also, the user is able to easily determine a sleep state referring to the indexes.

In addition, it is possible for the sleep state measuring apparatus 100 according to the embodiment to obtain the above mentioned indexes. Therefore, the user is able to easily determine a sleep state referring to the indexes.

For example, referring to the indexes such as the healing degree and the sleeping rhythm index, the user can not only detect whether or not there are sleep disorders, but also assume whether the sleep disorders are due to psychological problems or the surroundings when the user suffers from the sleep disorders.

In addition, the sleep state measuring apparatus that performs the above-described process is not limited to an apparatus mounted on an arm or the like. For example, a PC, which is capable of performing communication with a pulse wave sensor, may be used as the sleep state measuring apparatus.

In addition, the present invention is not limited to the above-described first embodiment, but various modifications are possible as exemplified below.

The sleep state measuring apparatus 100 according to the first embodiment is not limited to obtain an autonomic nerve index from a pulse wave. However, the same measurement is possible using an electrocardiogram, for example. In a modification of the first embodiment, an example in which an electrocardiogram is used will be described. A sleep state measuring apparatus according to the modification is connected to an electrocardiographic sensor instead of the pulse wave sensor. The sleep state measuring apparatus obtains electrocardiographic signals by the electrocardiographic sensor, and calculates heart beats every one beat. The modification has the same subsequent process as the first embodiment, other than the fact that a heart beat is used instead of a pulse, and thus a description thereof will be omitted.

The sleep state measuring apparatus 100 according to the first embodiment displays the obtained indexes on the display unit 102. However, the first embodiment is not limited to display the indexes on the display unit 102 provided at the sleep state measuring apparatus 100. However, the indexes may be displayed on an information processing device such as a PC which is capable of performing communication with a sleep state measuring apparatus. Here, the information processing device may perform a part of the processes. Therefore, in a second embodiment, a sleep state measuring apparatus and a sleep state measuring system formed of a PC will be described.

Figure 12:
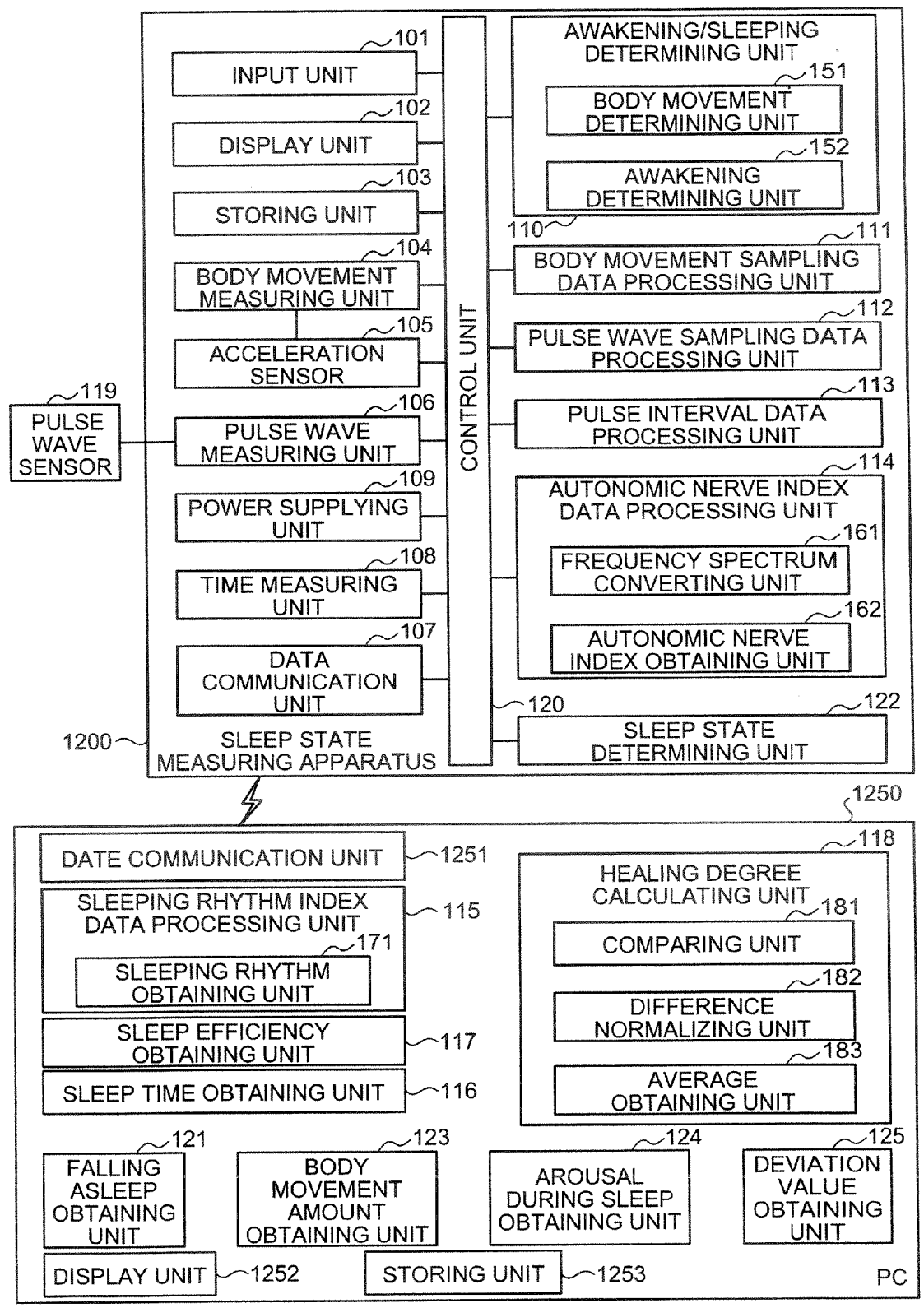
FIG. 12 is a block diagram illustrating a configuration of a sleep state measuring system according to a second embodiment.

FIG. 12 is a block diagram illustrating a configuration of a sleep state measuring system according to a second embodiment. The sleep state measuring system according to the present embodiment includes a sleep state measuring apparatus 1200 and a PC 1250. In the sleep state measuring system according to the second embodiment, the sleep state measuring apparatus 1200 obtains autonomic nerve indexes LF and HF through a measurement of a pulse wave, and transmits the obtained indexes LF and HF to the PC 1250. The PC 1250 analyzes the received autonomic nerve indexes LF and HF, obtains indexes such as a sleeping rhythm index or healing degree, and displays the obtained indexes on a radar chart.

The sleep state measuring apparatus 1200 is different from the sleep state measuring apparatus 100 according to the first embodiment in that the configuration for obtaining each of the indexes is excluded.

The PC 1250 includes the sleep state determining unit 122, the sleeping rhythm index data processing unit 115, the sleep time obtaining unit 116, the sleep efficiency obtaining unit 117, the healing degree calculating unit 118, the falling asleep obtaining unit 121, the body movement amount obtaining unit 123, the arousal during sleep obtaining unit 124, and the deviation value obtaining value 125, which are the configuration for obtaining each of indexes in the sleep state measuring apparatus 100 according to the first embodiment. Further, the PC 1250 includes a data communication unit 1251, a display unit 1252, and a storing unit 1253. Here, the description of the configuration of the sleep state measuring system of the present embodiment, which is the same as that of the sleep state measuring apparatus 100, is not repeated.

First, the configuration of the sleep state measuring apparatus 1200 will be described. The display unit 102 displays a state while measuring sleep, a result of a sleep state, such as awakening or REM sleep, or the like.

The storing unit 103 stores data which shows a result of user's sleep measurement, such as measurement data, e.g., pulse wave data and body movement data, and pulse interval data, a threshold value for determining a sleep state, and data of the determined sleep state.

The data communication unit 107 performs reception and transmission of data from/to the PC 1250. In the present embodiment, the data communication unit 107 transmits the obtained autonomic nerve indexes LF and HF, body movement data, and awakening/sleeping data to the PC 1250. In addition, the data communication unit 107 transmits the same to the PC every predetermined time (e.g., every one minute).

Next, the configuration of the PC 1250 will be described. The data communication unit 1251 performs reception and transmission of data from/to the sleep state measuring apparatus 1200.

The display unit 1252 displays a result of measuring of a sleep state in a radar chart. A detailed example of a screen is not repeated because the display unit 1252 has the same screen as the display unit 102 according to the first embodiment. In addition, in the present embodiment, the display unit 1252 uses a display connected to the PC. However, the display unit 1252 may be formed of any one of all display means generally used.

The storing unit 1253 stores data, such as falling asleep, sleep time, sleep efficiency, healing degree, a sleeping rhythm index, body movement, arousal during sleep obtained by analyzing with PC.

In addition, the sleep state measuring system of the present embodiment is not limited to the above-described configuration. For example, the sleep state measuring system may include the configuration according to the first embodiment, in which the sleep state measuring apparatus includes the sleeping rhythm index data processing unit 115 or the healing degree calculating unit 118 so as to obtain indexes. Further, the PC may include the display unit that displays the indexes, and the data communication unit.

In another example, the sleep state measuring apparatus may have the configuration in which the process up to the data-processing of a pulse wave is performed. The PC may obtain autonomic nerve indexes and obtains other indexes based on the obtained autonomic nerve indexes. In the sleep state measuring system, any one of the sleep state measuring apparatus and the PC which construct the system may include the above-described configuration.

In addition, the sleep state measuring system according to the present embodiment is not limited to measuring a sleep state by using the acceleration sensor and the pulse wave sensor. However, the sleep state may be measured by using another sensor as shown in an embodiment to be described later.

The sleep state measuring system according to the present embodiment can obtain the same effects as the sleep state measuring apparatus according to the first embodiment. In addition, in the sleep state measuring system, the respective indexes are displayed as the radar chart or the like in the display unit 1252 of the PC 1250. For this reason, it is possible to display the indexes in detail. Therefore, it is easy to check the respective indexes. In addition, when the process is performed by two apparatuses, that is, the sleeping measuring apparatus and the PC, the process when the indexes are calculated is divided up. Therefore, loads in each of the apparatuses can be reduced.

The sleep state measuring apparatus is not limited to measuring various kinds of indexes indicating a sleep state by using the acceleration sensor and the pulse wave sensor like the first and second embodiments, and another measuring apparatus may be used for measurement. For example, a pressure sensor measures vibration of user's chest or abdomen, detects heart beats and body movement, and measures a sleep state based on the measured data. Therefore, in a sleep state measuring apparatus according to a third embodiment, a case in which measurement is performed by using a mat-type sensor module will be described.

Figure 13:
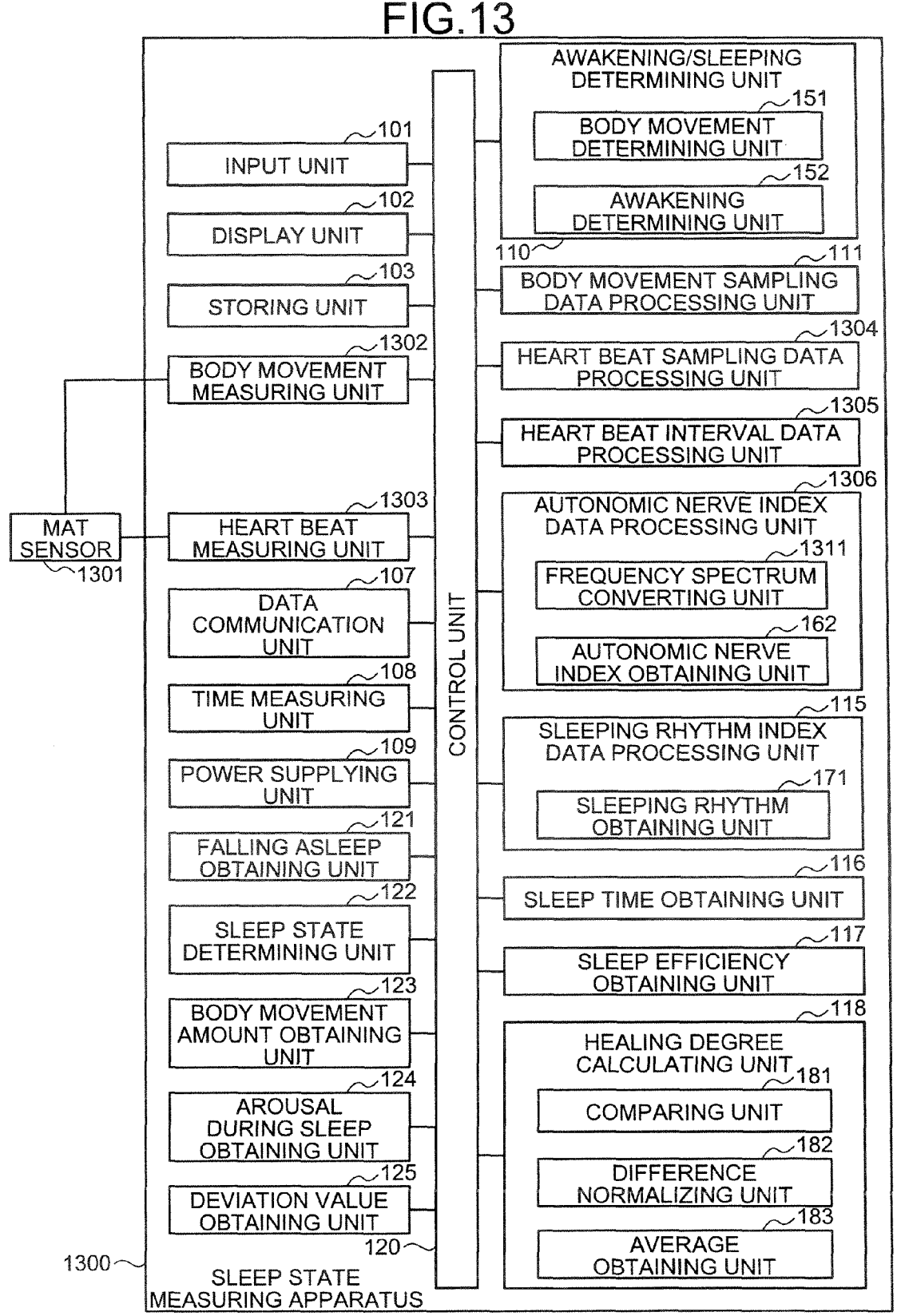
FIG. 13 is a block diagram illustrating a configuration of a sleep state measuring apparatus according to a third embodiment.

FIG. 13 is a block diagram illustrating a configuration of a sleep state measuring apparatus 1300 according to a third embodiment. The sleep state measuring apparatus 1300 is different from the sleep state measuring apparatus 100 as follows. A mat sensor 1301 is added instead of the pulse wave sensor 119. A body movement measuring unit 1302, which performs a different process from the body movement measuring unit 104, is provided. A heart beat measuring unit 1303 is provided instead of the pulse wave measuring unit 106. A heart beat sampling data processing unit 1304, which processes a different target from the pulse wave sampling data processing unit 112, is provided. A heart beat sampling data processing unit 1304, which processes a different target from the pulse wave sampling data processing unit 112, is provided. A heart beat interval data processing unit 1305, which processes a different target from the pulse interval data processing unit 113, is provided. An autonomic nerve index data processing unit 1306, which processes a different target from the autonomic nerve index data processing unit 114, is provided. In addition, a description of the configuration in the sleep state measuring apparatus 1300 according to the present embodiment, which is the same as that in the sleep state measuring apparatus 100 according to the first embodiment, is not repeated.

The mat sensor 1301 detects vibration of user's chest or abdomen by a mat-type pressure sensor module. In addition, the mat sensor 1301 may detect vibration by which user's absence, presence in a bed, body movement, and the like can be measured. The mat sensor 1301 in the present embodiment is a piezoelectric element which is formed in a shape of a tape by forming high molecular piezoelectric material, such as polyvinylidene fluoride, in a shape of thin film and attaching flexible electrode layers to both sides of the thin film. In addition, when detecting the vibration of the user's chest or abdomen, the mat sensor 1301 outputs detected signals to the body movement measuring unit 1302 and the heart beat measuring unit 1303.

Figure 14:
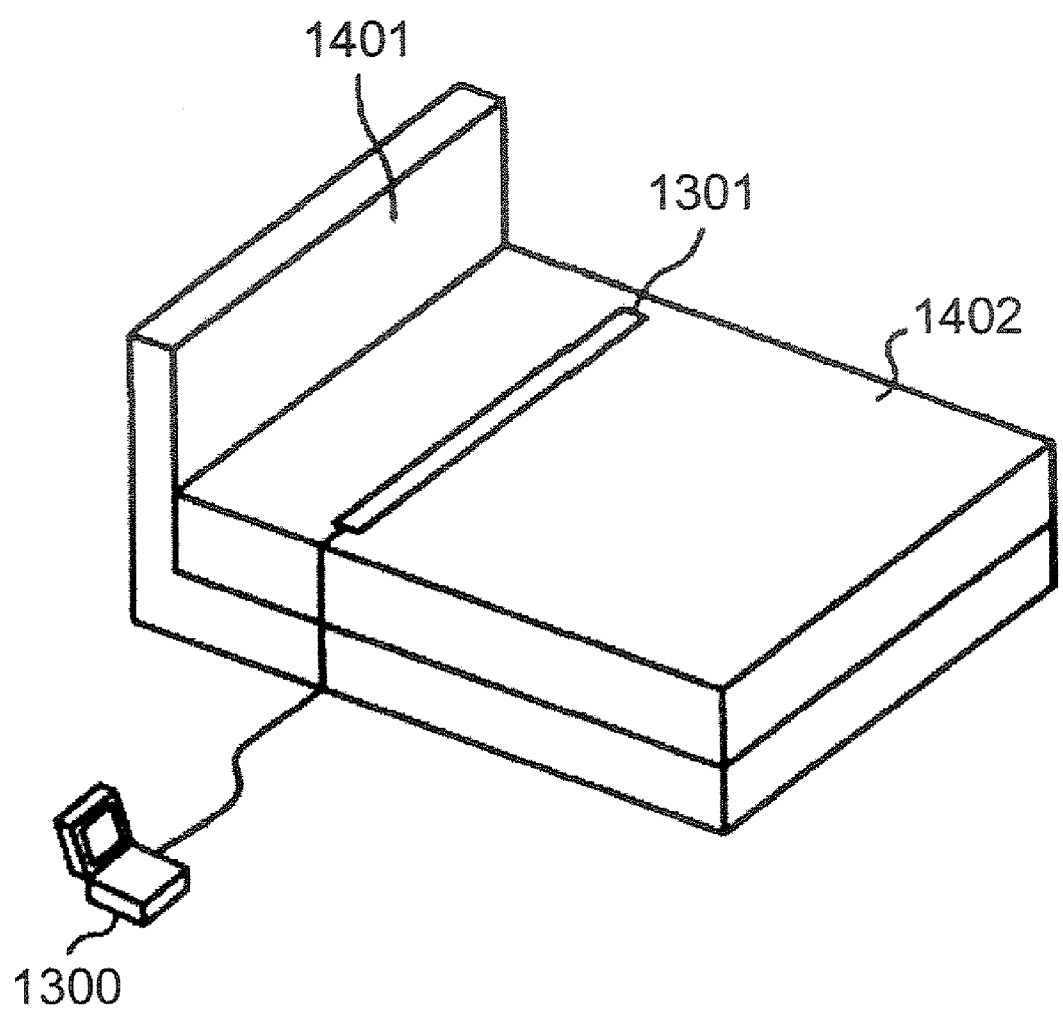
FIG. 14 is a view illustrating an example in which the mat sensor of the sleep state measuring apparatus according to the third embodiment is disposed.

FIG. 14 is a view illustrating an example in which the mat sensor 1301 of the sleep state measuring apparatus 1300 according to the present embodiment is disposed. As show therein, the mat sensor 1301 is provided on the surface of a mattress 1402 of a bed 1401 so as to detect vibration of the user's chest or abdomen.

Returning to FIG. 13, the body movement measuring unit 1302 measures user's body movement based on the detected signals input from the mat sensor 1301. In the present embodiment, the body movement measuring unit 1302 measures the user's body movement by extracting bands of the signals, which show the body movement, according to filtering, and performing conversion to a digital quantity according to A/D converter after passing an amplifier. Like the first embodiment, the measured body movement is processed by the body movement sampling data processing unit 111.

The heart beat measuring unit 1303 measures user's heart beats based on the detected signals input from the mat sensor 1301. In the present embodiment, the heart beat measuring unit 1303 measures the user's heart beats by extracting bands of the detected signals, which show heart beats, according to filtering, and performing conversion to a digital quantity according to A/D converter after passing an amplifier.

The heart beat sampling data processing unit 1304 and the heart beat interval data processing unit 1305 perform substantially the same processes as the pulse wave sampling data processing unit 112 and the pulse interval data processing unit 113, respectively, according to the first embodiment, except for the fact that a target to be processed in the present embodiment is a heart beat, not a pulse wave. Therefore, descriptions thereof are not repeated.

The autonomic nerve index data processing unit 1306 corresponds to the autonomic nerve index data processing unit 114 except for the fact that a frequency spectrum converting unit 1311, which processes a different target from the frequency spectrum converting unit 161, is provided. Therefore, a description thereof is not repeated. The frequency spectrum converting unit 1311 converts a series of heart beat interval data, processed by the heart beat interval data processing unit 1305, into frequency spectrum distribution according to an analysis method such as a fast fourier transform (FFT), instead of the pulse interval data according to the first embodiment.

The above-described sleep state measuring apparatus 1300 according to the third embodiment can obtain the same effects as the first embodiment. In addition, the sleeping measuring apparatus 1300 according to the third embodiment can perform measurement without being directly mounted on the user. Therefore, it is possible for the user to measure indexes in a comfortable environment.

Figure 15:
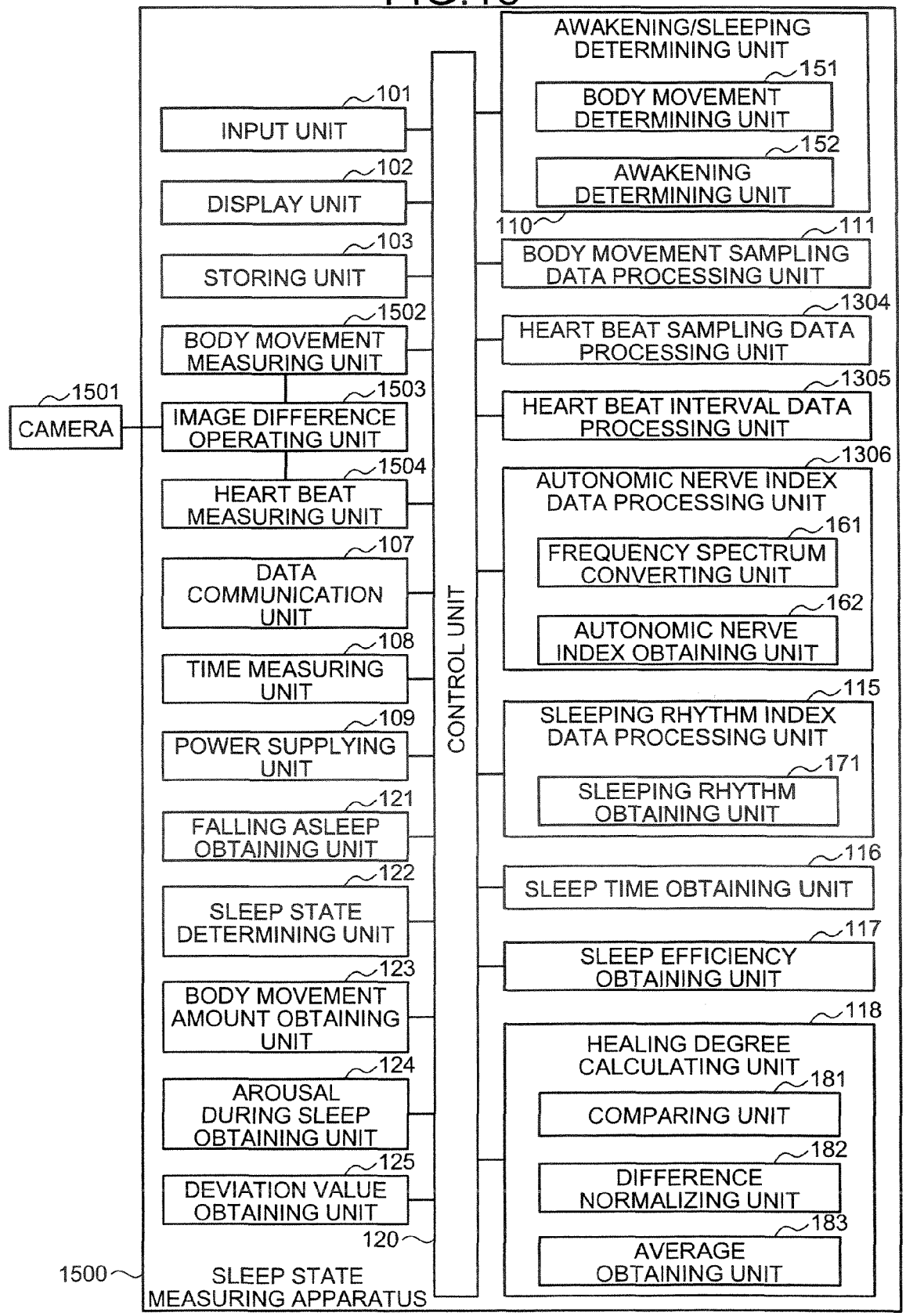
FIG. 15 is a block diagram illustrating a configuration of a sleep state measuring apparatus according to a fourth embodiment.

FIG. 15 is a block diagram illustrating a configuration of a sleep state measuring apparatus 1500 according to a fourth embodiment. The sleep state measuring apparatus 1500 according to the fourth embodiment is different from the sleep state measuring apparatus 1300 according to the third embodiment as follows. The mat sensor 1301 is excluded in the fourth embodiment. Instead, a camera 1501 and an image difference operating unit 1503 are added. Further, a body movement measuring unit 1502, which performs a different process from the body movement measuring unit 1302, is provided. A heart beat measuring unit 1504, which performs a different process from the heart beat measuring unit 1303, is provided. In addition, a description of the configuration of the sleep state measuring apparatus 1500, which is the same as that of the sleep state measuring apparatus 1300 according to the third embodiment, is not repeated. The sleep state measuring apparatus 1500 according to the present embodiment measures indexes indicating a sleep state based on users' images captured by the camera 1501.

The camera 1501 captures images by which user's movements can be detected. In the embodiment, the camera 1501 captures images of a blanket covering the user. The image difference operating unit 1503 calculates a difference between the captured images according to every frame in a direction of time, and calculates the sum at each pixel so as to obtain a value according to the displacement amount. The blanket covering the user is slightly displaced in synchronization with user's breathing or heart beats. For this reason, the values according to the displacement amount, obtained based on the difference of the captured images of the blanket, is a value in which values indicating user's breathing, heart beats and body movement overlap one another. Accordingly, the heart beats and the body movement can be measured by analyzing the value according to the displacement amount.

The body movement measuring unit 1502 measures user's body movement based on the value according to the displacement amount obtained by the image difference operating unit 1503. In the embodiment, with respect to the input value according to the displacement amount, the body movement measuring unit 1502 measures user's body movement by performing filtering in a band showing the body movement, amplification by an amplifier and A/D conversion to a digital quantity.

The heart beat measuring unit 1504 measures user's heart beats based on the value according to the displace amount obtained by the image difference operating unit 1503. In the embodiment, the heart beat measuring unit 1504 performs filtering in a band showing the heart beats, amplification by an amplifier and A/D conversion to a digital quantity with respect to the input value according to the displacement amount, which is obtained by the image difference operating unit 1503, so as to measure user's heart beats.

As described above, the sleep state measuring apparatus 1500 according to the present embodiment can obtain the same effects as the third embodiment by performing the same process as the sleep state measuring apparatus 1300 according to the third embodiment after detecting the heart beats and the body movement based on the images captured by the camera 1501.

In addition, the present invention is not limited to the above-described embodiment, but various modifications are possible as exemplified below for the embodiment.

The sleep state measuring apparatus and the sleep state measuring system according to the above-described embodiment is not limited to displaying indexes indicating a sleep state in a radar chart. Therefore, in a first modification, the sleep state measuring apparatus or a PC connected to the sleep state measuring apparatus displays respective indexes indicating a sleep state in a bar graph.

Figure 16:
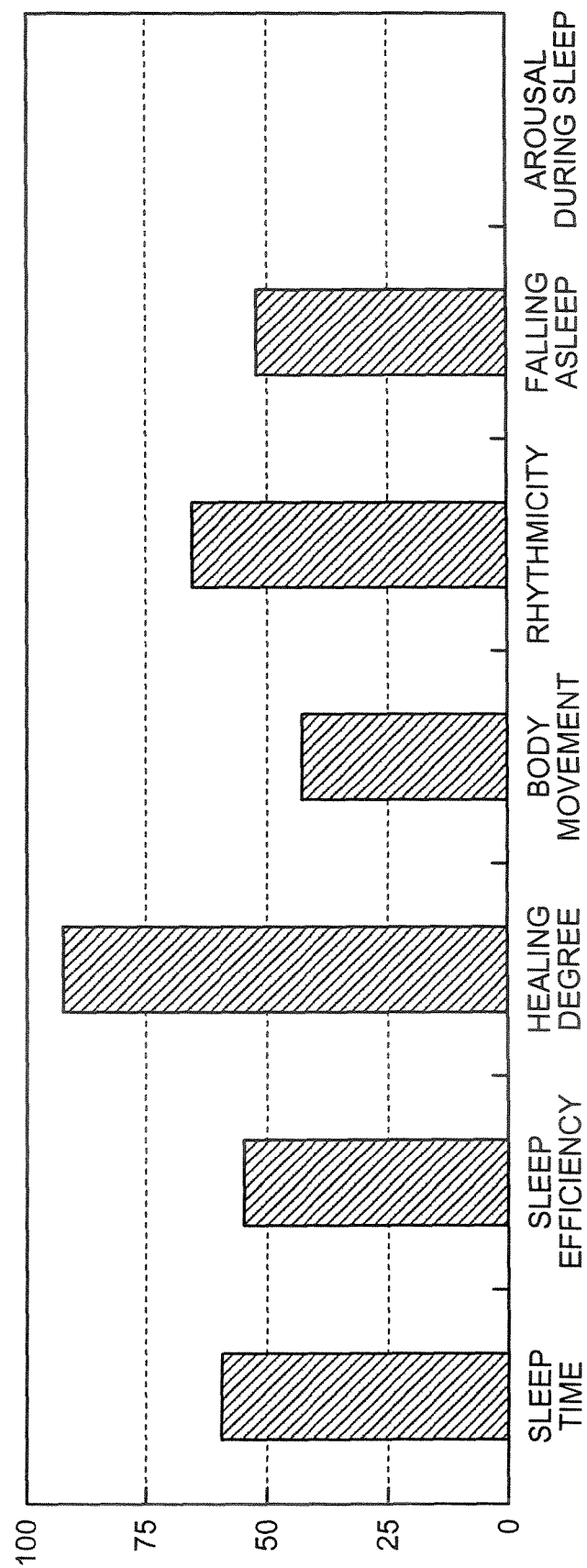
FIG. 16 is a view illustrating one example of a bar graph showing a measuring result of sleeping which is displayed by a sleep state measuring apparatus or a display unit of a PC according to a first modification.

FIG. 16 is a view illustrating one example of a bar graph showing a measuring result of sleeping which is displayed by a sleep state measuring apparatus or a display unit of a PC. As shown therein, the deviation values according to the respective indexes, which are obtained by the deviation value obtaining unit 125, can be displayed in a bar graph on the display unit 102. Accordingly, it is possible for the user to understand his or her sleep state in detail same as the radar chart.

In addition, the indexes indicating the sleep state may be displayed in other forms in addition to the radar chart or the bar graph. For example, the respective indexes may be displayed according to steps of degree such as "smile, normal, cry" in facial expressions of animals or the like.

In addition, LF and HF are used as autonomic nerve indexes in the above-described embodiment. However, other indexes used as autonomic nerve indexes may be calculated based on heart beats. For example, RR50 which reflects a parasympathetic nerve or a heart beat standard deviation which reflects a sympathetic nerve may be used as an autonomic nerve index. RR50 is an index which reflects fluctuation in a state of parasympathetic nerve dominance, and is counted up when a difference between an instantaneous pulse interval per beat of a predetermined range (one minute) and the preceding instantaneous pulse interval becomes 50 milliseconds or more. In addition, the heart beat standard deviation may be used as a sympathetic nerve index because the heart beat standard deviation reflects fluctuation of the sympathetic nerve to some extent, and degree of the deviation is equivalent to LF.

As described above, the apparatus, method and system of measuring sleep state according to the present invention are useful as techniques for measuring a user's sleep state, and particularly, are suitable for the user to easily determine a sleep state.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sleep state measuring apparatus, comprising:
an autonomic nerve index obtaining unit that obtains a user's autonomic nerve index by measuring a user and obtains a temporal change of the autonomic nerve index according to a time lapse; and
a sleep periodicity index calculating unit that calculates a sleep periodicity index based on a difference between the temporal change of the autonomic nerve index and a change of a time function showing a user's sleeping cycle, wherein the sleep periodicity index indicates whether the user is sleeping or not according to a periodic sleeping cycle as an index,
wherein the sleep periodicity index calculating unit includes a sleeping cycle obtaining unit that determines a parameter of a cosine or sine function which has a minimum error with respect to the change of the autonomic nerve index, and obtains the cosine or sine function using the parameter as the time function showing the user's sleeping cycle.

2. The apparatus according to claim 1 further comprising:
a body movement measuring unit that measures user's body movement;
a sleeping determining unit that determines whether the user is sleeping or not based on the body movement;
a sleep time obtaining unit that obtains information on user's sleep time based on a result of determining whether the user is sleeping or not;
a sleep efficiency obtaining unit that obtains information on user's sleep efficiency based on a result of determining whether the user is sleeping or not; and
a sleep information maintaining unit that correlates and maintains the sleep periodicity index and any one or more of the sleep time information and the sleep efficiency information.

3. The apparatus according to claim 2 further comprising:
a sleeping result display processing unit that displays the correlated and maintained sleep periodicity index and any one or more of the sleep time information and the sleep efficiency information as deviation values.

4. The apparatus according to claim 3, wherein the sleeping result display processing unit displays the deviation values in a radar chart.

5. The apparatus according to claim 3, wherein the sleeping result display processing unit displays the deviation values in a bar graph.

6. The apparatus according to claim 1, further comprising:
a heart beat interval detecting unit that detects a user's pulse or heart beat,
wherein the autonomic nerve index obtaining unit obtains the autonomic nerve index based on a change in the pulse or heart beat.

7. The apparatus according to claim 6, wherein the heart beat interval detecting unit includes a pulse wave measuring unit that measures a pulse wave based on a change in user's peripheral bloodstream, and the beat detecting unit detects a pulse from the pulse wave.

8. The sleep state measuring apparatus according to claim 6, wherein the beat detecting unit detects a heart beat from electrocardiographic signals input from an electrocardiographic sensor.

9. The apparatus according to claim 6, wherein the beat detecting unit includes a pressure change measuring unit that measures a change in user's body pressure, and the beat detecting unit detects a heart beat based on the change in the user's body pressure.

10. The apparatus according to claim 6, wherein the beat detecting unit includes an image capturing unit that captures images of the user, and the beat detecting unit detects a heart beat based on temporal change in the captured images of the user.

11. A method of measuring a sleep state, comprising:
obtaining a user's autonomic nerve index by measuring a user and obtaining a temporal change of the autonomic nerve index according to a time lapse;
determining a parameter of a cosine or sine function which has the minimum error with respect to the change of the autonomic nerve index to obtain the cosine or sine function using the parameter as a time function showing a user's sleeping cycle; and
calculating a sleep periodicity index based on a difference between the temporal change of the autonomic nerve index and a change of the time function showing a user's sleeping cycle, wherein the sleep periodicity index indicates whether the user is sleeping or not according to a periodic sleeping cycle as an index.

12. A system of measuring a sleep state comprising:
a sleep state measuring apparatus that performs a measurement of a user; and
an information processing apparatus that communicates with the sleep state measuring apparatus,
wherein the sleep state measuring apparatus includes
an autonomic nerve index obtaining unit that obtains a user's autonomic nerve index by measuring the user and obtains a temporal change of the autonomic nerve index according to a time lapse; and
a data transmitting unit that transmits the autonomic nerve index, and
the information processing apparatus includes
a data receiving unit that receives the autonomic nerve index; and
a sleep periodicity index calculating unit that calculates a sleep periodicity index based on a difference between the temporal change of the autonomic nerve index and a change of a time function showing a user's sleeping cycle, wherein the sleep periodicity index indicates whether the user is sleeping or not according to a periodic sleeping cycle as an index,
wherein the sleep periodicity index calculating unit includes a sleeping cycle obtaining unit that determines a parameter of a cosine or sine function which has the minimum error with respect to the change of the autonomic nerve index and obtains the cosine or sine function using the parameter as the time function showing the user's sleeping cycle.

\* \* \* \* \*